(12) United States Patent
Tang et al.

(10) Patent No.: US 12,075,698 B2
(45) Date of Patent: Aug. 27, 2024

(54) ELECTROLUMINSCENT MATERIAL CONTAINING CARBONYL GROUP, AND APPLICATION THEREOF TO OLED

(71) Applicant: South China University of Technology, Guangzhou (CN)

(72) Inventors: Ben Zhong Tang, Guangzhou (CN); Zujin Zhao, Guangzhou (CN); Huijun Liu, Guangzhou (CN); Anjun Qin, Guangzhou (CN); Rongrong Hu, Guangzhou (CN); Zhiming Wang, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 911 days.

(21) Appl. No.: 17/048,373

(22) PCT Filed: Oct. 25, 2018

(86) PCT No.: PCT/CN2018/111933
§ 371 (c)(1),
(2) Date: Oct. 16, 2020

(87) PCT Pub. No.: WO2019/200875
PCT Pub. Date: Oct. 24, 2019

(65) Prior Publication Data
US 2021/0376251 A1    Dec. 2, 2021

(30) Foreign Application Priority Data
Apr. 16, 2018 (CN) .......................... 201810339446.5

(51) Int. Cl.
*H10K 85/60*    (2023.01)
*C07D 401/14*    (2006.01)
(Continued)

(52) U.S. Cl.
CPC ....... *H10K 85/6572* (2023.02); *C07D 401/14* (2013.01); *C07D 413/14* (2013.01);
(Continued)

(58) Field of Classification Search
CPC .... C07D 401/14; C07D 413/14; C09K 11/06; C09K 2211/1007; C09K 2211/1018;
(Continued)

(56) References Cited

FOREIGN PATENT DOCUMENTS

| CN | 106279203 A | 1/2017 |
|---|---|---|
| CN | 107068880 A | 8/2017 |

(Continued)

OTHER PUBLICATIONS

Supporting Information, Robust Luminescent Materials with Prominent Aggregation-Induced Emission and Thermally Activated Delayed Fluorescence for High-Performance Organic Light-Emitting Diodes, Chemistry of Materials, vol. 29, Mar. 31, 2017 (Year: 2017).*
(Continued)

*Primary Examiner* — Sarah Pihonak
*Assistant Examiner* — Padmaja S Rao
(74) *Attorney, Agent, or Firm* — LOZA & LOZA LLP; Michael Fedrick

(57) ABSTRACT

The disclosure belongs to the technical field of organic photoelectric materials, and discloses carbonyl containing organic electroluminescent materials and use thereof in OLED. The carbonyl containing organic electroluminescent materials have a structure of formula I, wherein $R_1$ and $R_2$ are different in Formula I, $R_1$ and $R_2$ are different electron-donating groups of aromatic ring derivatives; $R_1$ is an electron-donating groups of hole transport host materials or electron-donating groups of bipolar transport host materials. The luminescent materials of the present disclosure are organic electroluminescent materials based on derivatives of
(Continued)

a host material and a benzoyl group. They have both AIE and delayed fluorescence characteristics with high-efficiency solid-state emission, high exciton utilization, and bipolar features. The organic electroluminescent device prepared by the organic electroluminescent materials of the present disclosure has very good performance and broad application prospect in the field of organic electroluminescence.

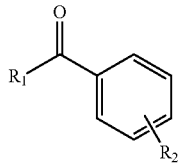

Formula I

7 Claims, 4 Drawing Sheets

(51) Int. Cl.
C07D 413/14 (2006.01)
C09K 11/06 (2006.01)
H10K 50/11 (2023.01)
(52) U.S. Cl.
CPC ............ *C09K 11/06* (2013.01); *H10K 85/636* (2023.02); *H10K 85/657* (2023.02); *C09K 2211/1007* (2013.01); *C09K 2211/1018* (2013.01); *H10K 50/11* (2023.02)
(58) Field of Classification Search
CPC .... C09K 2211/1029; C09K 2211/1033; H10K 2101/20; H10K 50/11; H10K 85/636; H10K 85/657; H10K 85/6572; H10K 50/00
See application file for complete search history.

(56) References Cited

FOREIGN PATENT DOCUMENTS

CN 107641117 A 1/2018
CN 2019200875 A1 10/2019

OTHER PUBLICATIONS

Supporting Information, Highly Efficient Nondoped OLEDs with Negligible Efficiency Roll-Off Fabricated from Aggregation-Induced Delayed Fluorescence Luminogens, Angewandte Chemie International Edition, vol. 56, Sep. 13, 2017 (Year: 2017).*
Jingjing Guo et al., Achieving High-Performance Nondoped OLEDs with Extremely Small Efficiency Roll-Off by Combining Aggregation-Induced Emission and Thermally Activated Delayed Fluorescence, Advanced Science News, 2017, pp. 1-9, WILEY-VCH Verlag Gmbh & Co. KGaA, Weinheim.
Jian Huang et al., Highly Efficient Nondoped OLEDs with Negligible Efficiency Roll-Off Fabricated from Aggregation-Induced Delayed Fluorescence Luminogens, A Journal of the Gesellschaft Deutscher Chemiker Angewandte Chemie International Edition, 10.1002/anie.201706752, WILEY-VCH Verlag Gmbh & Co. KGaA, Weinheim.
Huijun Liu et al., A Versatile Molecular Design for High-Performance Nondoped OLEDs with ~100% Exciton Utilization and Negligible Efficiency Roll-Off, Angewandte Chemie International Edition, 10.1002/anie.201802060, WILEY-VCH Verlag Gmbh & Co. KGaA, Weinheim.
Jingjing Guo, Robust Luminescent Materials with Prominent Aggregation-Induced Emission and Thermally Activated Delayed Fluorescence for High-Performance Organic Light-Emitting Diodes, Chemistry of Materials, Apr. 1, 2017, pp. 1-11, American Chemical Society Publications, Washington, D.C.
International Search Report for International Application No. PCT/CN2018/111933.

* cited by examiner

ELECTROLUMINSCENT MATERIAL CONTAINING CARBONYL GROUP, AND APPLICATION THEREOF TO OLED

CROSS-REFERENCE TO RELATED APPLICATIONS

This application is a National Phase application claiming the benefit of International Application No PCT/CN2018/111933 filed Oct. 25, 2018, which claims priority to Chinese Patent Application No. CN 201810339446.5, filed Apr. 16, 2018, the complete disclosures of which are hereby incorporated in by reference in their entireties.

TECHNICAL FIELD

This disclosure belongs to the technical field of organic photoelectric materials, and particularly relates to carbonyl containing organic electroluminescent materials and use thereof in the field of organic electroluminescence.

BACKGROUND

Organic electroluminescent devices, also known as organic light-emitting diodes (OLEDs), are devices that convert electrical energy into light energy based on organic semiconductor materials. Following the pioneering work of Dr. Deng Qingyun and others in 1987, OLEDs have shown broad application prospects in flat panel displays and solid-state lighting, which has aroused great interest and widespread concern in the academic and industrial circles. The overall performance of OLEDs devices is directly related to organic light-emitting materials, and therefore the development of new and excellent organic electroluminescent materials has become a hotspot in the field of OLEDs.

In OLEDs based on traditional fluorescent materials, only 25% of singlet excitons can be used to emit light, and 75% of triplet excitons are dissipated in a non-radiative form, leading to the low efficiency of the OLEDs. In order to make full use of 75% of triplet excitons, researchers have developed a second generation of luminescent materials (transition metal complex phosphorescent materials). Doped OLED devices based on such phosphorescent materials can make use of singlet and triplet excitons at the same time, so the device efficiency is significantly improved. However, the phosphorescent materials containing heavy metals are expensive and have poor stability, and severe efficiency roll off severely, which limits its practical application in electroluminescent devices. In 2012, the group of Professor Adachi in Kyushu University developed a third generation of organic light-emitting materials, i.e., pure organic thermally activated delayed fluorescence (TADF) materials. In doped OLED devices, these materials can also make full use of the singlet and triplet excitons formed by electrical excitation with high device efficiency, but the efficiency roll-off is also severe, and so far there are only few available existing pure organic TADF materials. At the same time, these TADF materials may also be affected by the aggregation-caused quenching (ACQ) effect, resulting in low solid-state photoluminescent quantum yield and reduced performance of the devices.

In 2001, Ben Zhong Tang's research group reported a novel concept: in a single molecule state, some luminescent molecules may only emit light weakly, but after aggregation, the luminescence of these molecules is significantly enhanced, which is called "aggregation-induced emission" (AIE). This inspires a new idea for solving the ACQ problem of luminescent materials. Since then, more and more AIE materials with high-efficiency solid-state luminescence covering all visible light colors have been developed. Based on these materials, researchers have prepared relatively efficient non-doped OLEDs with simple device structures and low efficiency roll-off. However, these materials are usually fluorescent materials and can only emit light by singlet excitons. Thus, there is still much room for improvement in device efficiency.

Overview of the Disclosure

In order to overcome the above shortcomings and deficiencies of the prior art, a purpose of the present disclosure is a method and process to provide carbonyl containing organic electroluminescent materials. The material has both AIE and delayed fluorescence characteristics. This material emits weakly in a dilute solution where almost no delayed fluorescence is observed, but the luminescence is enhanced in an aggregate state and significant delayed fluorescence may be found. The organic electroluminescent material of the present disclosure has the characteristics of high-efficiency solid-state light emission, high electrogenerated exciton utilization and bipolarity, allowing the preparation of high EL efficiencies, low efficiency roll-offt and non-doped organic electroluminescent devices.

Another object of the present disclosure is to provide a method for preparing the above-mentioned carbonyl containing organic electroluminescent materials. The method of the present disclosure has the advantages of a novel process using easily obtained raw materials and high yield.

Another object of the present disclosure is to provide use of the above-mentioned carbonyl containing organic electroluminescent materials in the field of organic electroluminescence, especially in organic electroluminescent devices.

The purposes of the present disclosure are achieved through the following solutions:

Carbonyl containing organic electroluminescent materials have a structure as shown by formula I or formula II:

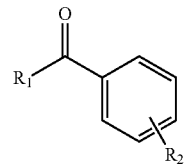

Formula I

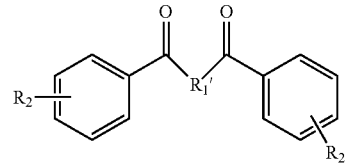

Formula II wherein $R_1$, $R_1'$ and $R_2$ are different electron-donating groups of aromatic ring derivatives. $R_1$ and $R_1'$ are electron-donating groups of host materials with hole transport ability or electron-donating groups of bipolar transport host materials.

The R₁ is one of the following structures 1 to 32:
1
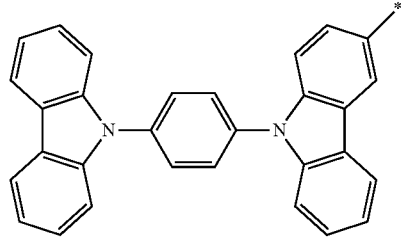
2
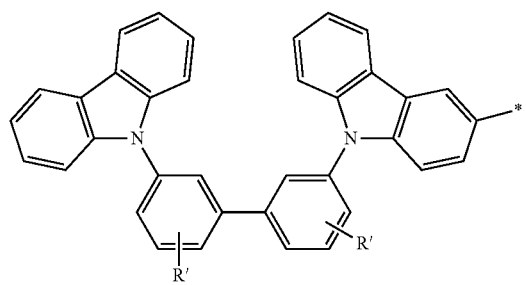
3
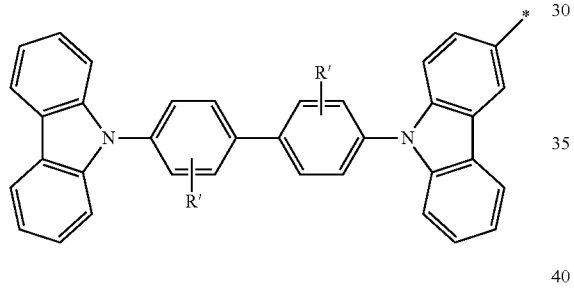
4
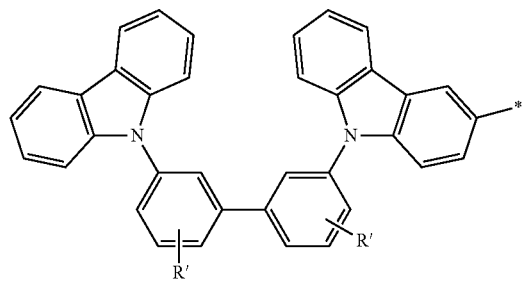
5
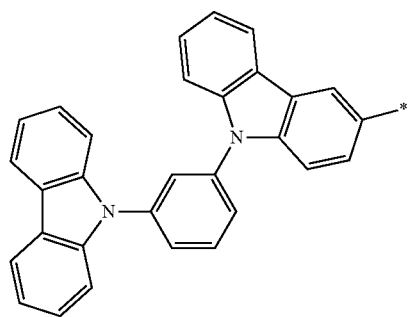
6
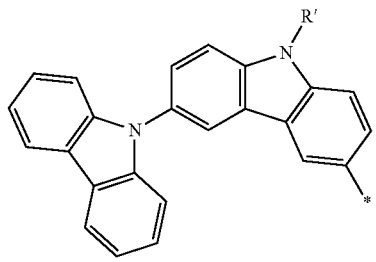
7
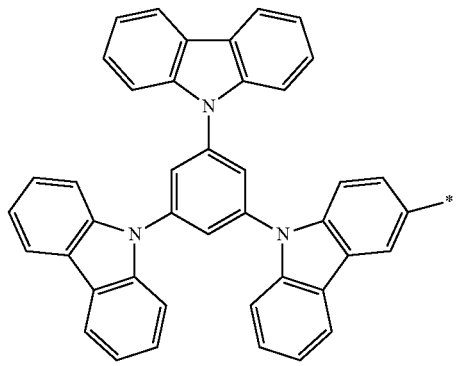
8
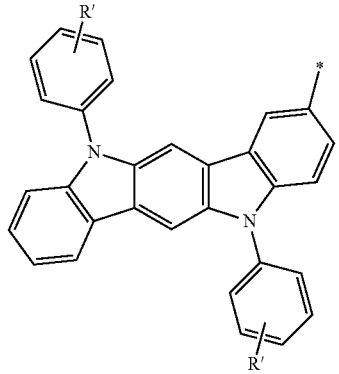
9
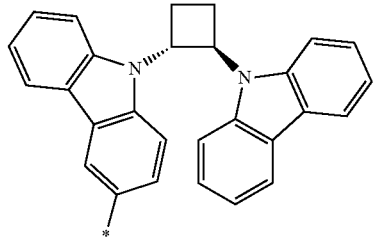
10
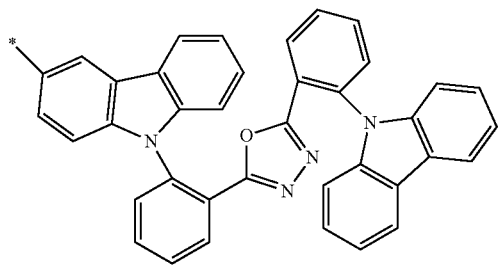

11
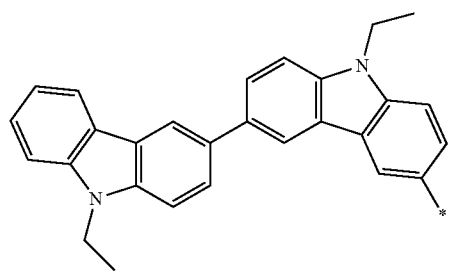
12
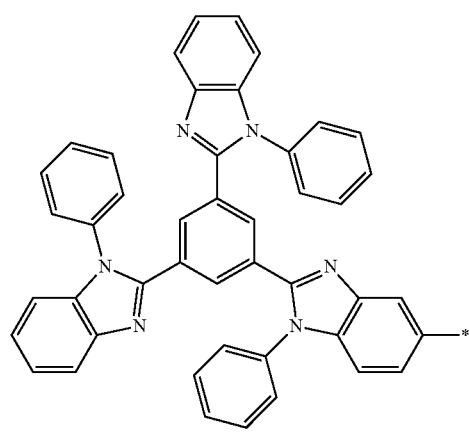
13
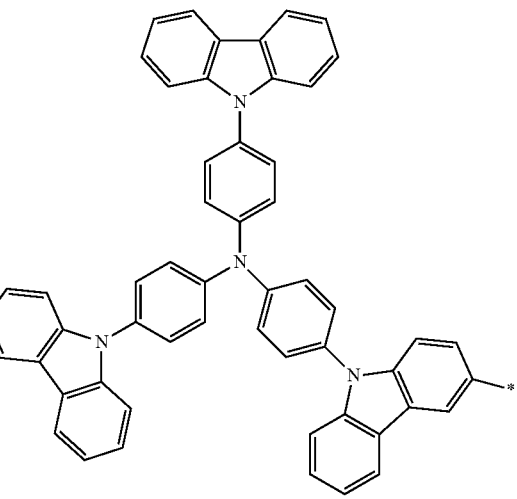
14
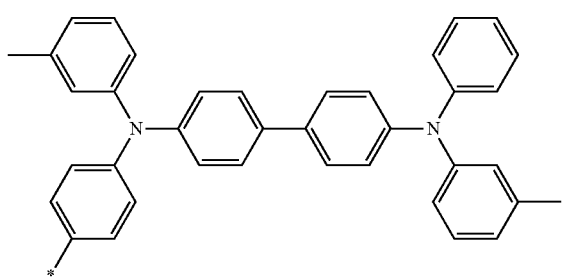
15
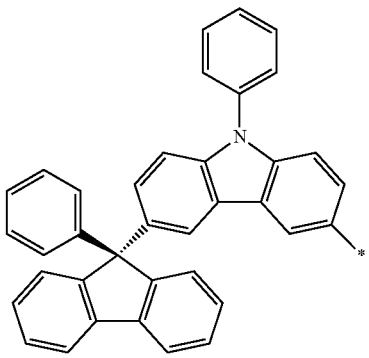
16
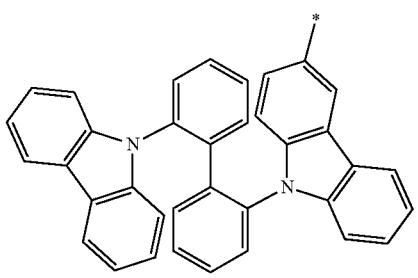
17
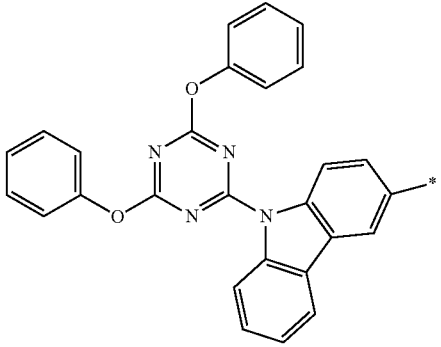
18
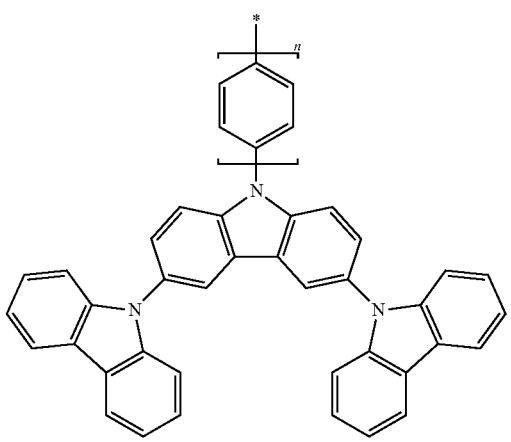

19
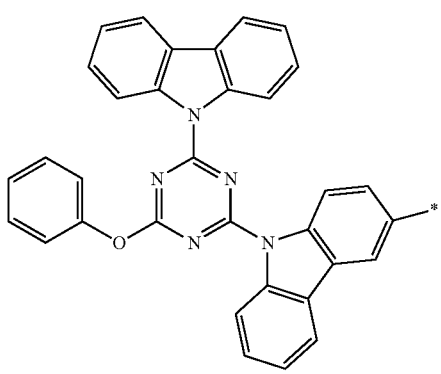
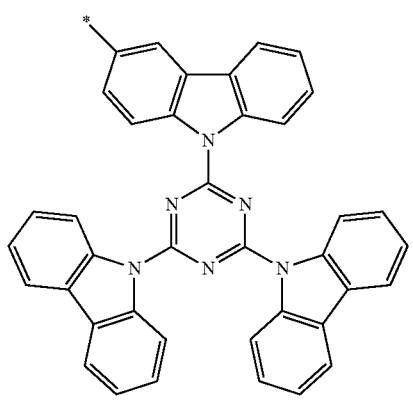
21 X = CH₂
22 X = O
23
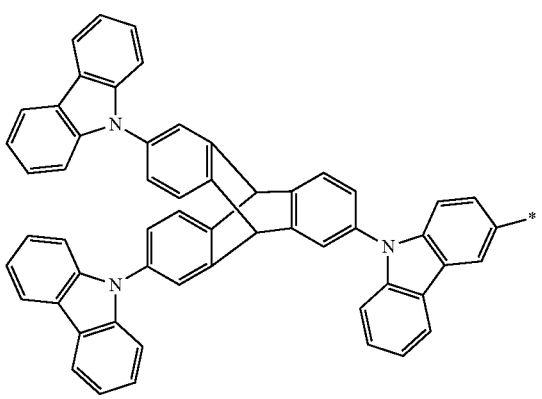
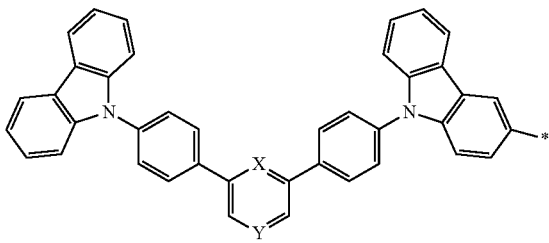
24 X = CH, Y = N
26 X = N, Y = CH
26
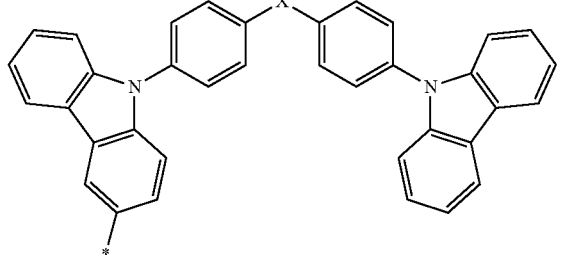
27
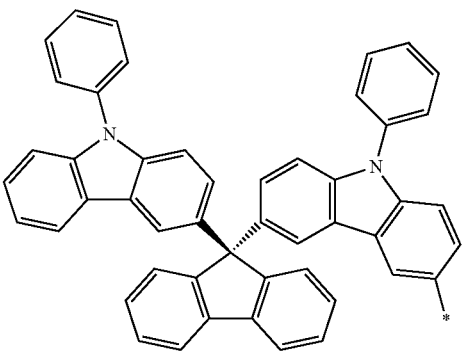
28
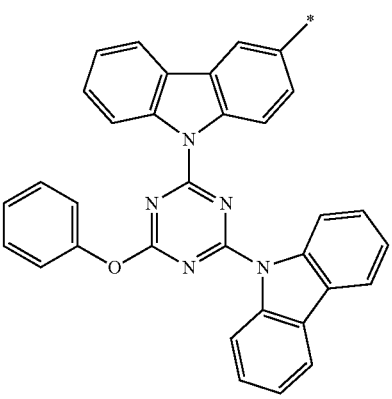

29.
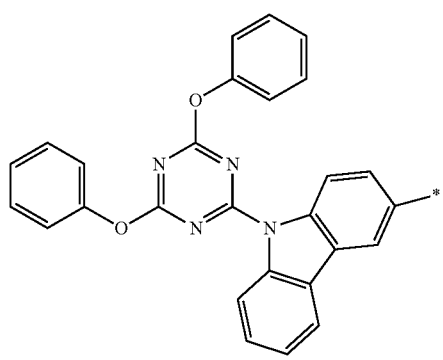
30.
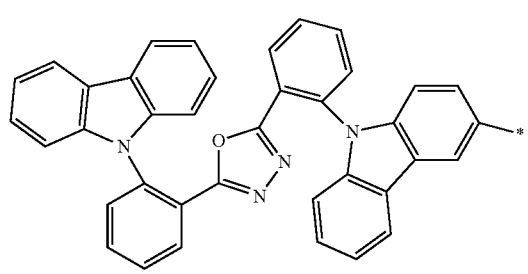
31.
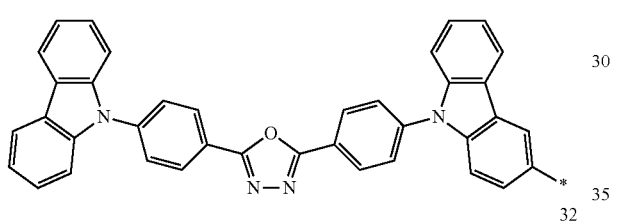
32.
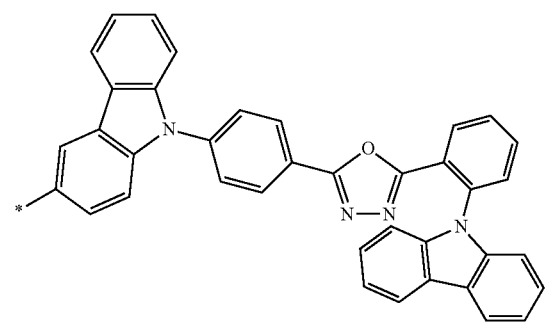
Wherein R' is hydrogen or alkyl chain, and n is a natural number between 0 and 10.
The $R_1'$ has a structure of any of structures 33-57:
33.
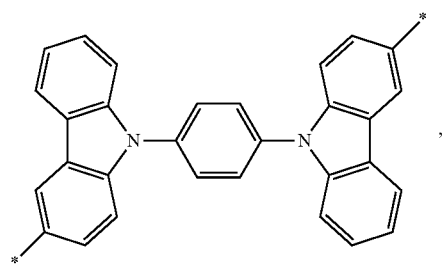
34.
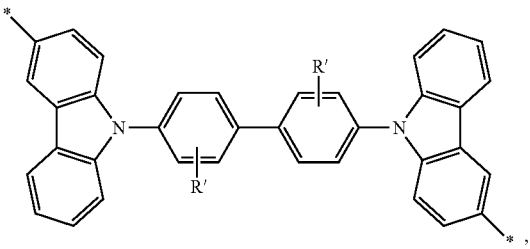
35.
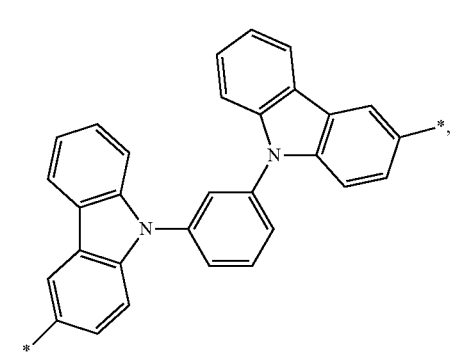
36.
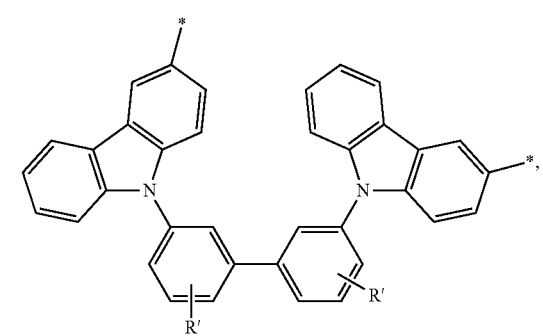
37.
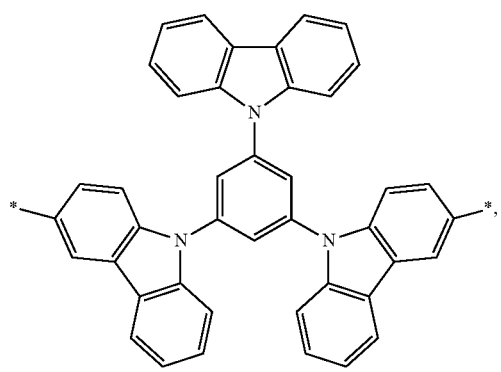

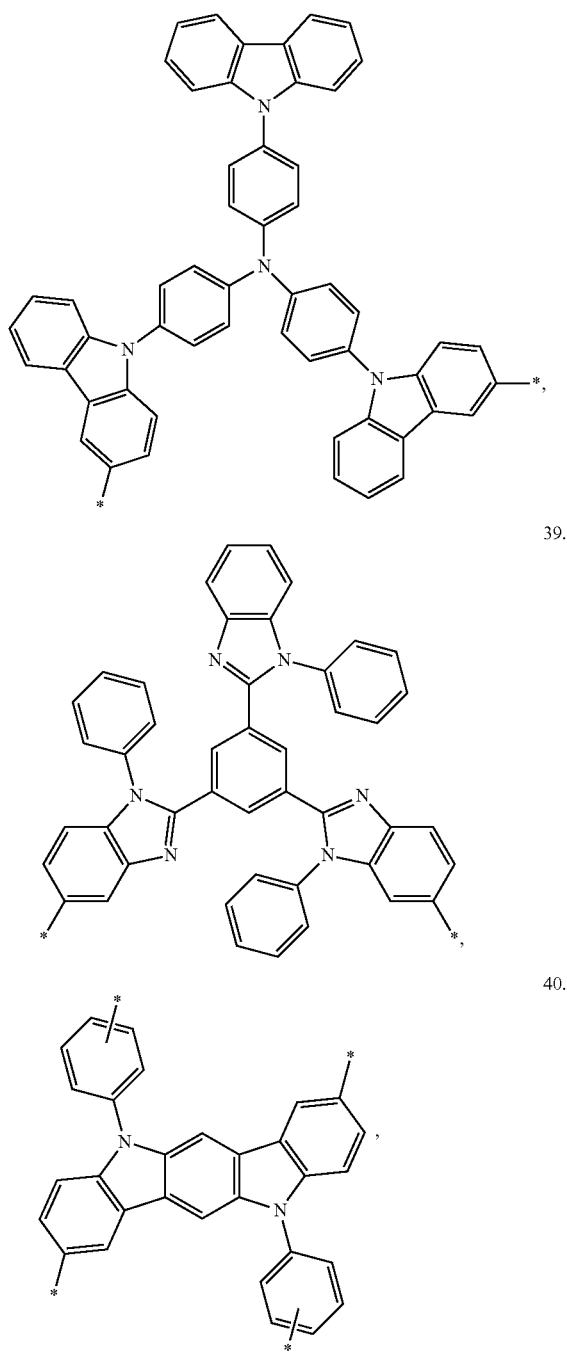
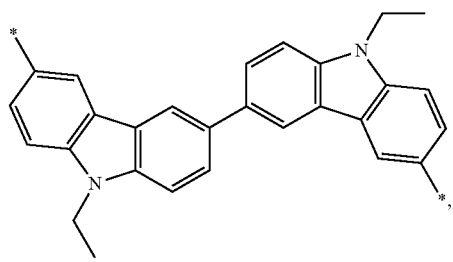
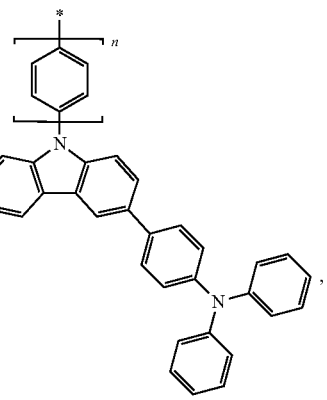
43. X = CH$_2$
44. X = O
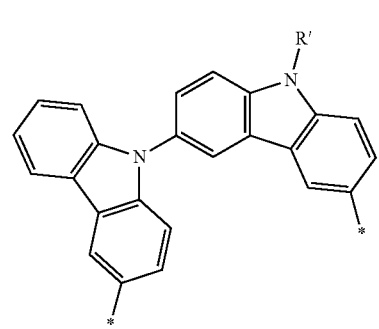
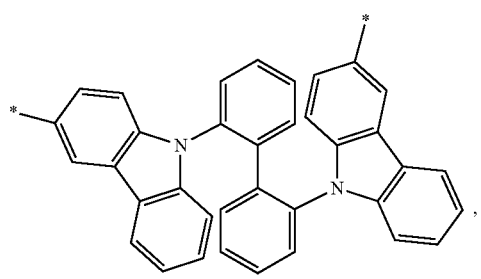

47.
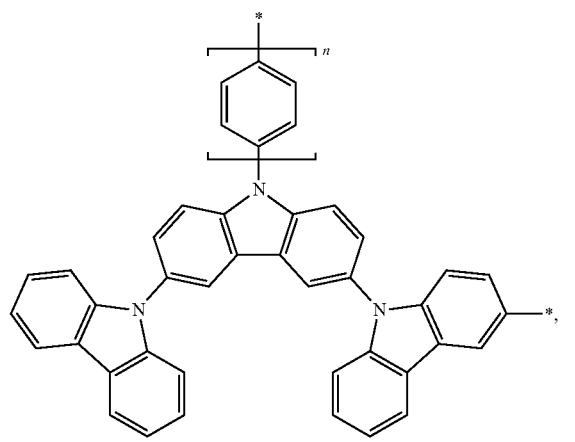
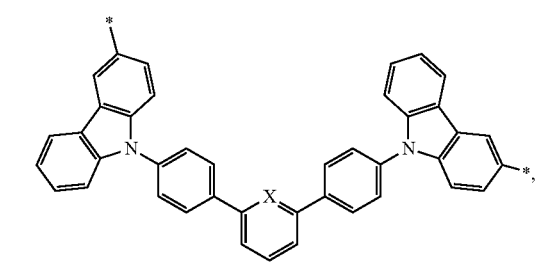
48. X = CH, Y = N
49. X = N, Y = CH
50.
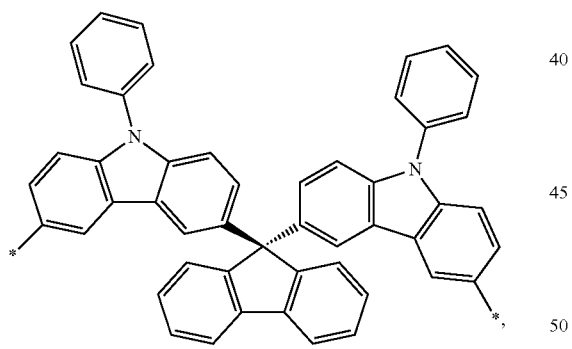
51.
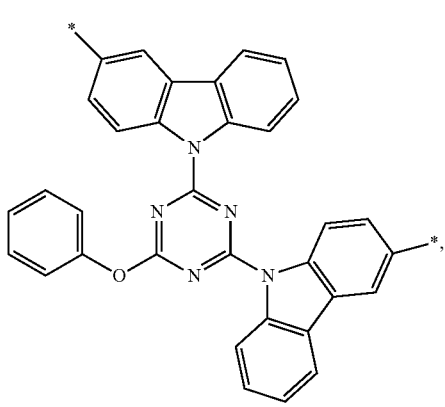
52.
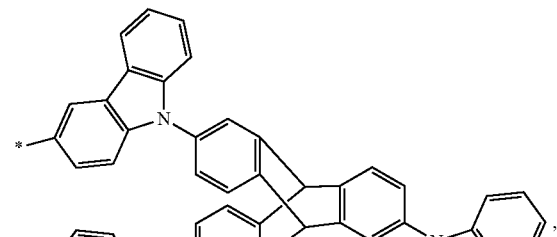
53.
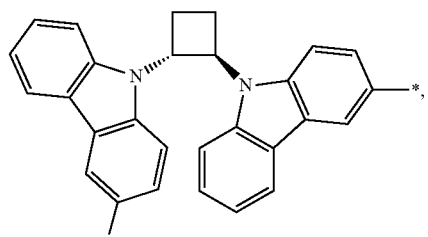
54.
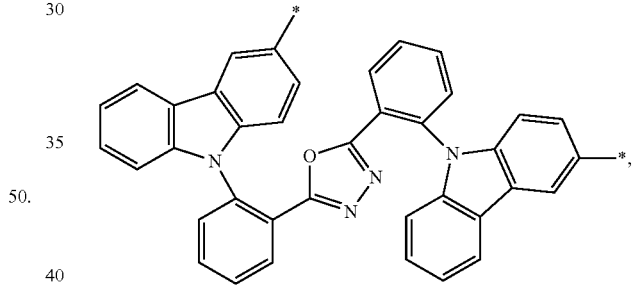
55.
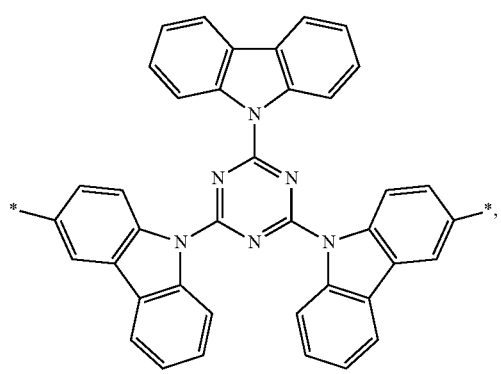
56.
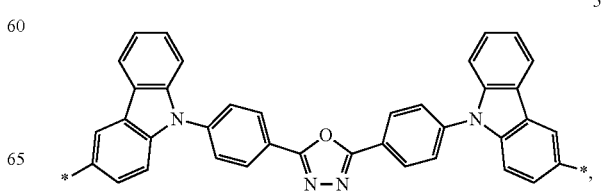

Wherein R' is hydrogen or alkyl group, and n is a natural number between 0 and 10.

The R₂ has a structure of any of structures a-o:

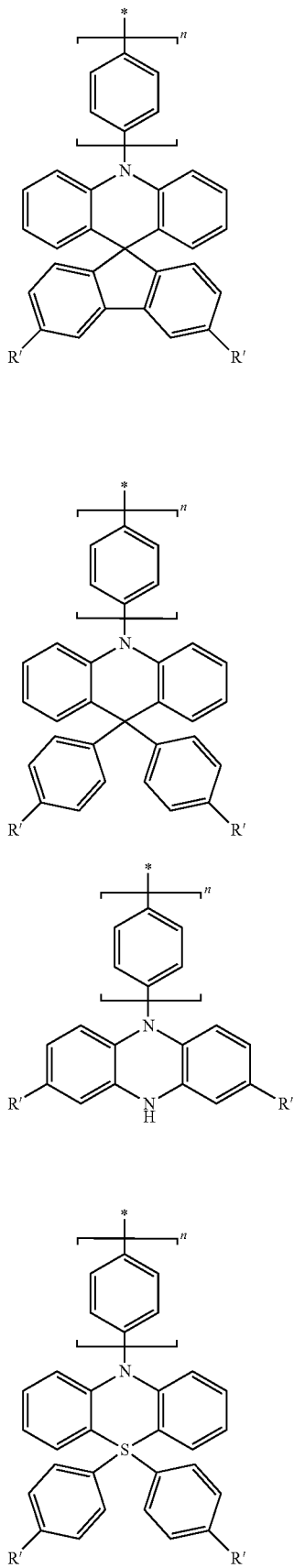

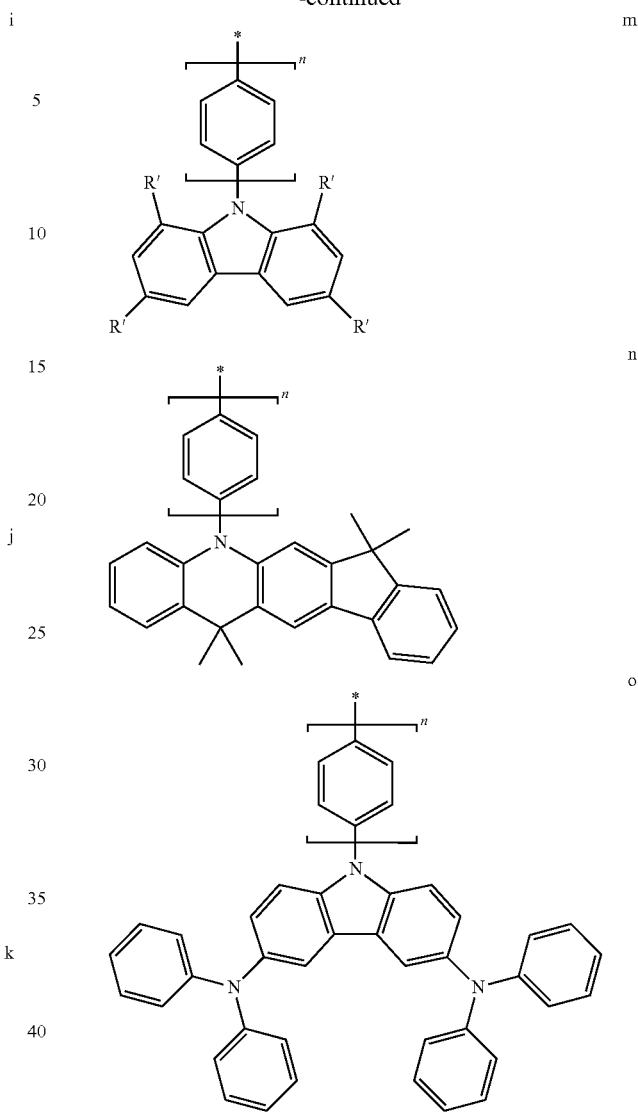

Wherein R' is hydrogen or alkyl group, and n is a natural number between 0 and 10.

The $R_1$ and $R_1'$ containing compounds provided by the present disclosure are both host materials for preparing organic electroluminescent devices, including hole transport host materials with electron donating groups or bipolar transport host materials with both electron donating and electron withdrawing groups. These groups have excellent charge transport properties, which may improve the performance of electroluminescent devices. $R_1$ and $R_1'$ represent monosubstitution and bisubstitution, respectively. $R_2$ is a commonly used electron-donating group for aromatic ring derivatives.

The preparation method of the above-mentioned carbonyl containing organic electroluminescent materials may comprises the following exemplary steps: using p-fluorobenzoyl chloride and aromatic derivatives $R_1H$ or $HR_1{}^1H$ as raw materials, obtaining organic fluoride through Friedel-Crafts reaction; under the action of a strong base catalyst, carrying out a reaction between the organic fluoride and an aromatic derivative $R_2H$ to obtain the carbonyl containing organic electroluminescent materials; wherein $R_1$ and $R_1'$ in the $R_1H$ or $HR_1{}^1H$ correspond to the $R_1$ and $R_1'$ in Formula I and Formula II, respectively; and $R_2$ in the $R_2H$ corresponds to the $R_2$ in Formula I and Formula II.

The strong base catalyst comprises potassium tert-butoxide, sodium tert-butoxide, and strong base NaH.

In the present disclosure, by connecting different electron-donating groups on both sides of the benzoyl group, the resulting molecular structure is distorted to avoid strong π-π interaction among the molecules in an aggregated state; in addition, electron donating (D)-electron withdrawing (A) structure and the distorted molecular structure may separate the spatial distribution of the highest occupied molecular orbital (HOMO) and the lowest unoccupied molecular orbital (LUMO), so that the molecules may have a smaller singlet-triplet energy level difference ($\Delta E_{ST}$), and the resulting materials may have both the characteristics of AIE and delayed fluorescence; therefore, the material of the present disclosure exhibits features of high-efficiency solid-state emission, high exciton utilization, and bipolarity. Based on such materials, high ELefficiencies, low efficiency roll-off, and non-doped organic light-emitting diodes can be prepared, which have broad application prospects in the field of organic electroluminescence, especially in flat panel displays and solid-state lighting.

The material of the present disclosure makes full use of singlet and triplet excitons, effectively alleviating the annihilation of excitons in an aggregated state. Also, the simple and efficient preparation method, excellent thermal stability and electrochemical stability allow large-scale synthesis and purification of these materials, which shows their great development prospect.

Compared with the prior art, the present disclosure has at least the following advantages and beneficial effects:
(1) The carbonyl containing organic electroluminescent materials of the present disclosure has both AIE and delayed fluorescence characteristics with high-efficiency solid-state luminescence, high exciton utilization and bipolar properties, and may be used to prepare high efficiency, low efficiency roll-off, and non-doped OLED;
(2) The carbonyl containing organic electroluminescent materials of the present disclosure has a simple preparation method, easy-to-obtain raw materials, high yield, a stable structure and low storage requirement;
(3) The carbonyl containing organic electroluminescent materials of the present disclosure has excellent electroluminescence performance and can be widely used in fields such as organic electroluminescence.

DETAILED DESCRIPTION OF THE DISCLOSURE

Figure 1:
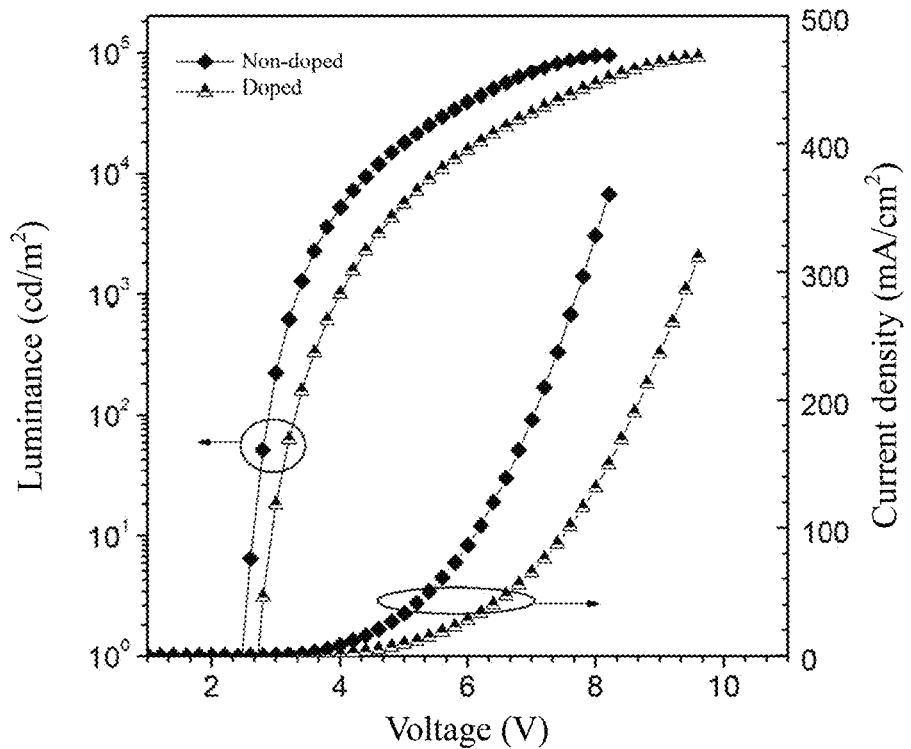
FIG. 1 is a J-V-L curve diagram of doped and undoped OLEDs prepared by the carbonyl containing organic electroluminescent materials in Example 1.

The present disclosure will be further described in detail below in conjunction with the examples and drawings, but the implementation and scope of the present disclosure is not limited thereto. The reagents used in the following examples are all commercially available.

Example 1: Preparation of Carbonyl Containing Organic Electroluminescent Material (DCB-BP-PXZ)

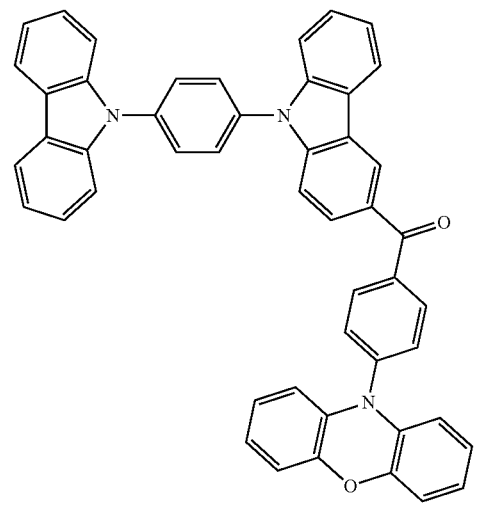 [SMILES: O=C(c1ccc(N2c3ccccc3Oc3ccccc32)cc1)c1ccc2c(c1)c1ccccc1n2-c1ccc(-n2c3ccccc3c3ccccc32)cc1]

The synthetic route was as follows:

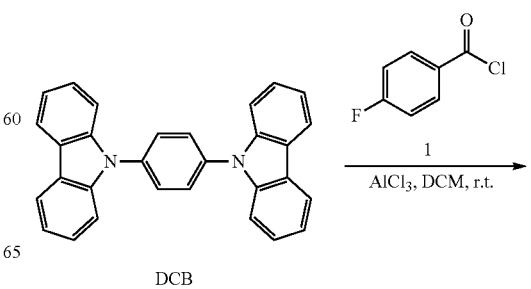

DCB

-continued

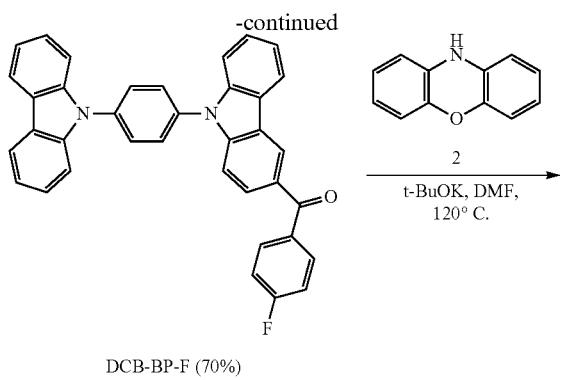

DCB-BP-F (70%)

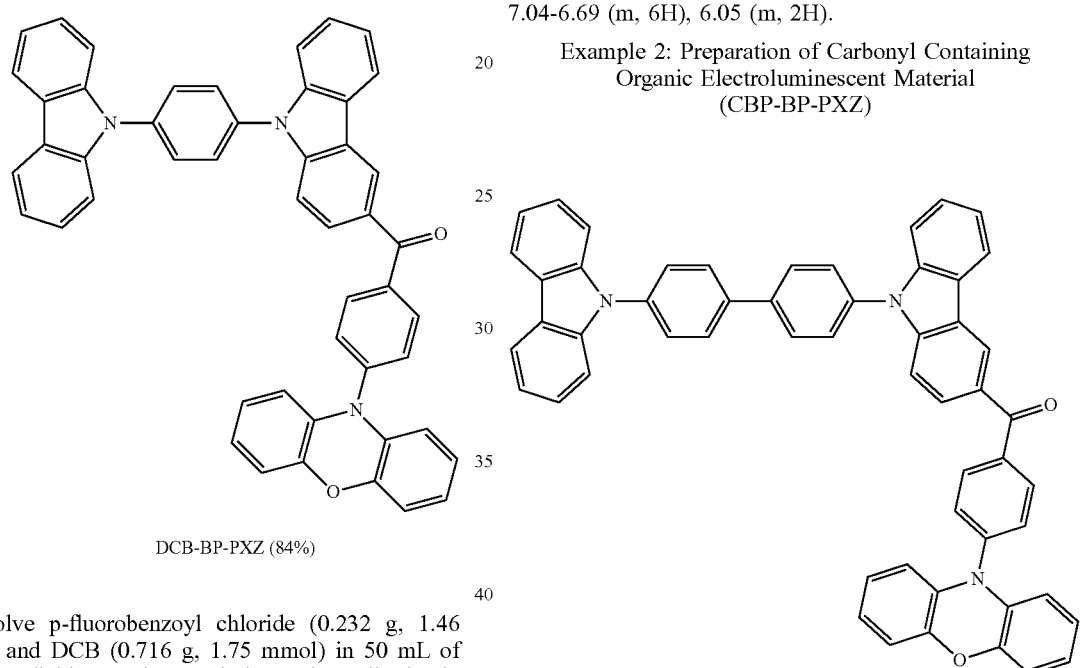

DCB-BP-PXZ (84%)

(1) Dissolve p-fluorobenzoyl chloride (0.232 g, 1.46 mmol) and DCB (0.716 g, 1.75 mmol) in 50 mL of ultra-dry dichloromethane solution, mix well, slowly add AlCl₃ (0.272 g, 2.04 mmol), and react at room temperature (in the synthetic route, r.t. means reaction in room temperature) for 3 hours; Then add ice-cold hydrochloric acid solution, extract the product with dichloromethane, concentrate the solution and conduct column chromatography to obtain a white solid DCB-BP-F with a yield of 70%;

(2) Dissolve the intermediate DCB-BP-F (0.36 g, 0.68 mmol) and phenoxazine (compound 2) (0.15 g, 0.81 mmol) in 20 mL of ultra-dry DMF, ventilate for three times, add t-BuOK (0.153 g, 1.36 mmol) under nitrogen protection, heat to 120° C., and react at this temperature for 12 hours. Then extract the product with dichloromethane and water, concentrate the solution and conduct column chromatography to obtain a yellow-green final product DCB-BP-PXZ, the yield being 84%.

$^1$H NMR (500 MHz, CDCl₃) δ 8.78 (s, 1H), 8.27 (d, J=10.3 Hz, 1H), 8.23-8.16 (m, 2H), 8.16-7.93 (m, 3H), 7.92-7.78 (m, 4H), 7.69-7.38 (m, 10H), 7.39-7.29 (m, 2H), 7.04-6.69 (m, 6H), 6.05 (m, 2H).

Example 2: Preparation of Carbonyl Containing Organic Electroluminescent Material (CBP-BP-PXZ)

The synthetic route was as follows:

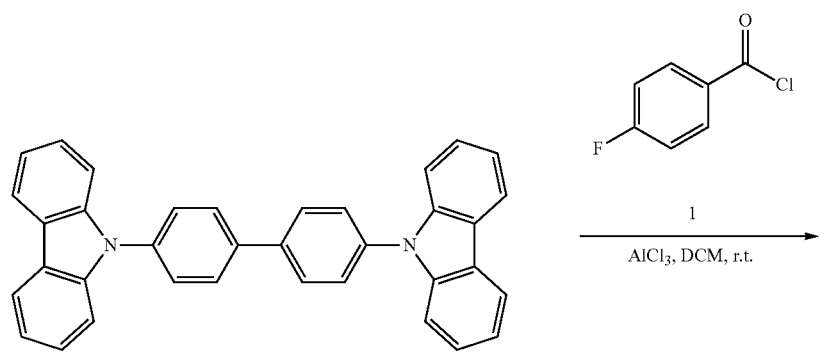

CBP

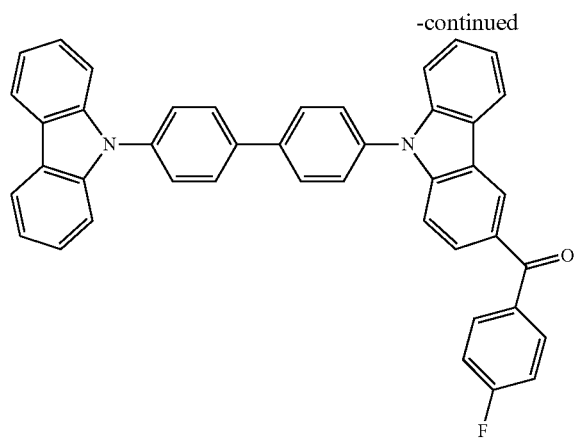
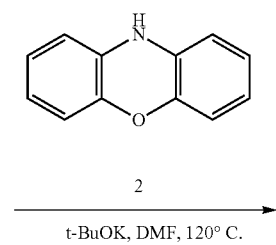
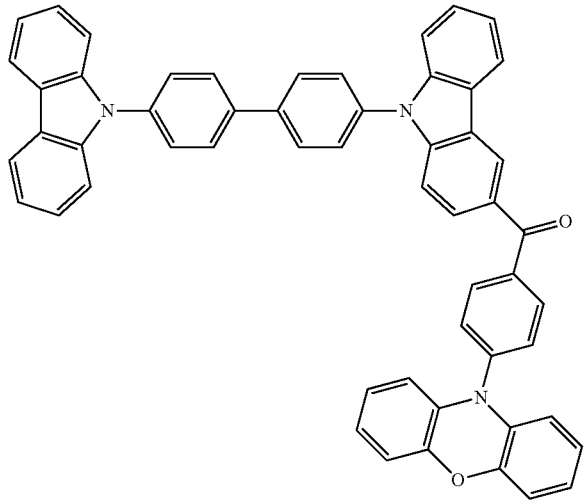

CBP-BP-PXZ (87%)

(1) Dissolve p-fluorobenzoyl chloride (0.476 g, 3.0 mmol) and CBP (1.745 g, 3.60 mmol) in 50 mL of ultra-dry dichloromethane solution, mix well, slowly add AlCl$_3$ (0.56 g, 4.2 mmol), and react at room temperature (in the synthetic route, r.t. means reaction in room temperature) for 3 hours; Then add ice-cold hydrochloric acid solution, extract the product with dichloromethane, concentrate the solution and conduct column chromatography to obtain a white solid CBP-BP-F with a yield of 75%;

(2) Dissolve the intermediate CBP-BP-F (0.728 g, 1.2 mmol) and phenoxazine (0.264 g, 1.44 mmol) in 20 mL of ultra-dry DMF, ventilate for three times, add t-BuOK (0.269 g, 2.4 mmol) under nitrogen protection, heat to 120° C., and react at this temperature for 12 hours. Then extract the product with dichloromethane and water, concentrate the solution and conduct column chromatography to obtain a yellow-green final product CBP-BP-PXZ, the yield being 87%.

$^1$H NMR (500 MHz, CDCl$_3$) δ 8.77 (s, 1H), 8.25 (d, J=7.8 Hz, 1H), 8.18 (d, J=7.7 Hz, 2H), 8.11 (d, J=7.9 Hz, 2H), 8.04 (d, J=8.6 Hz, 1H), 8.00-7.91 (m, 4H), 7.74 (d, J=7.9 Hz, 4H), 7.63-7.49 (m, 7H), 7.49-7.38 (m, 3H), 7.37-7.29 (m, 2H), 6.82-6.55 (m, 6H), 6.06 (m, 2H).

Example 3: Preparation of Carbonyl Containing Organic Electroluminescent Material (mCP-BP-PXZ)

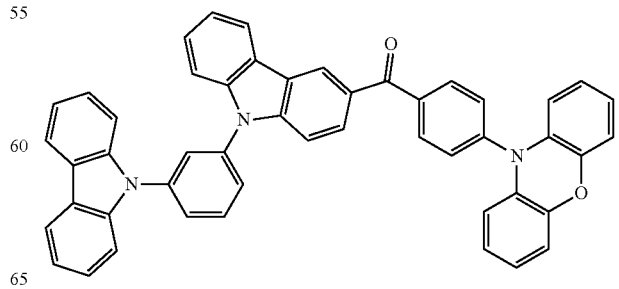

The synthetic route was as follows:

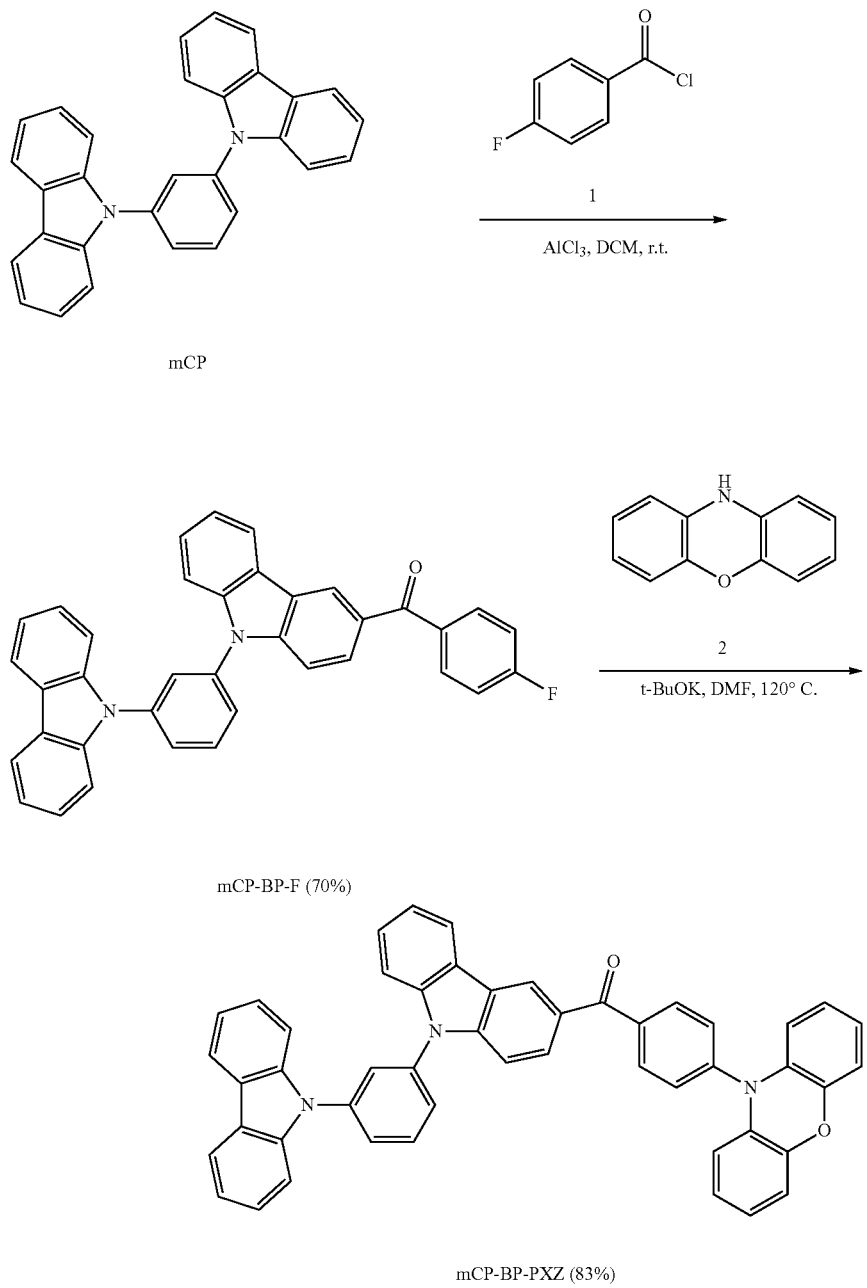

mCP mCP-BP-F (70%)

mCP-BP-PXZ (83%)

(1) Dissolve p-fluorobenzoyl chloride (1.11 g, 7.0 mmol) and mCP (3.43 g, 8.4 mmol) in 50 mL of ultra-dry dichloromethane solution, mix well, slowly add AlCl₃ (1.307 g, 9.8 mmol), and react at room temperature (in the synthetic route, r.t. means reaction in room temperature) for 3 hours; Then add ice-cold hydrochloric acid solution, extract the product with dichloromethane, concentrate the solution and conduct column chromatography to obtain a white solid mCP-BP-F with a yield of 70%;

(2) Dissolve the intermediate mCP-BP-F (0.739 g, 1.5 mmol) and phenoxazine (0.343 g, 1.875 mmol) in 20 mL of ultra-dry DMF, ventilate for three times, add t-BuOK (0.337 g, 3.0 mmol) under nitrogen protection, heat to 120° C., and react at this temperature for 12 hours. Then extract the product with dichloromethane and water, concentrate the solution and conduct column chromatography to obtain a yellow-green final product mCP-BP-PXZ, the yield being 83%.

$^1$H NMR (500 MHz, CDCl₃) δ 8.75 (d, J=1.3 Hz, 1H), 8.23 (d, J=7.7 Hz, 1H), 8.19-8.13 (m, 2H), 8.12-8.06 (m, 2H), 8.05-7.99 (m, 1H), 7.94-7.87 (m, 1H), 7.86-7.83 (m, 1H), 7.81-7.76 (m, 1H), 7.74-7.70 (m, 1H), 7.63-7.49 (m, 7H), 7.48-7.42 (m, 2H), 7.42-7.36 (m, 1H), 7.35-7.29 (m, 2H), 6.75-6.62 (m, 6H), 6.09-6.00 (m, 2H).

Example 4: Preparation of Carbonyl Containing Organic Electroluminescent Material (mCBP-BP-PXZ)
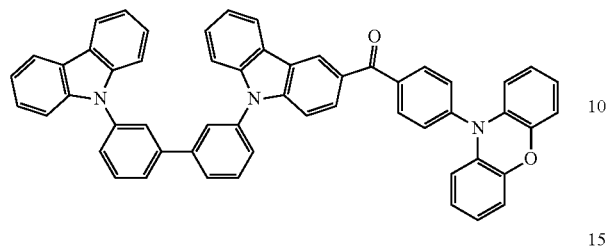
The synthetic route was as follows.
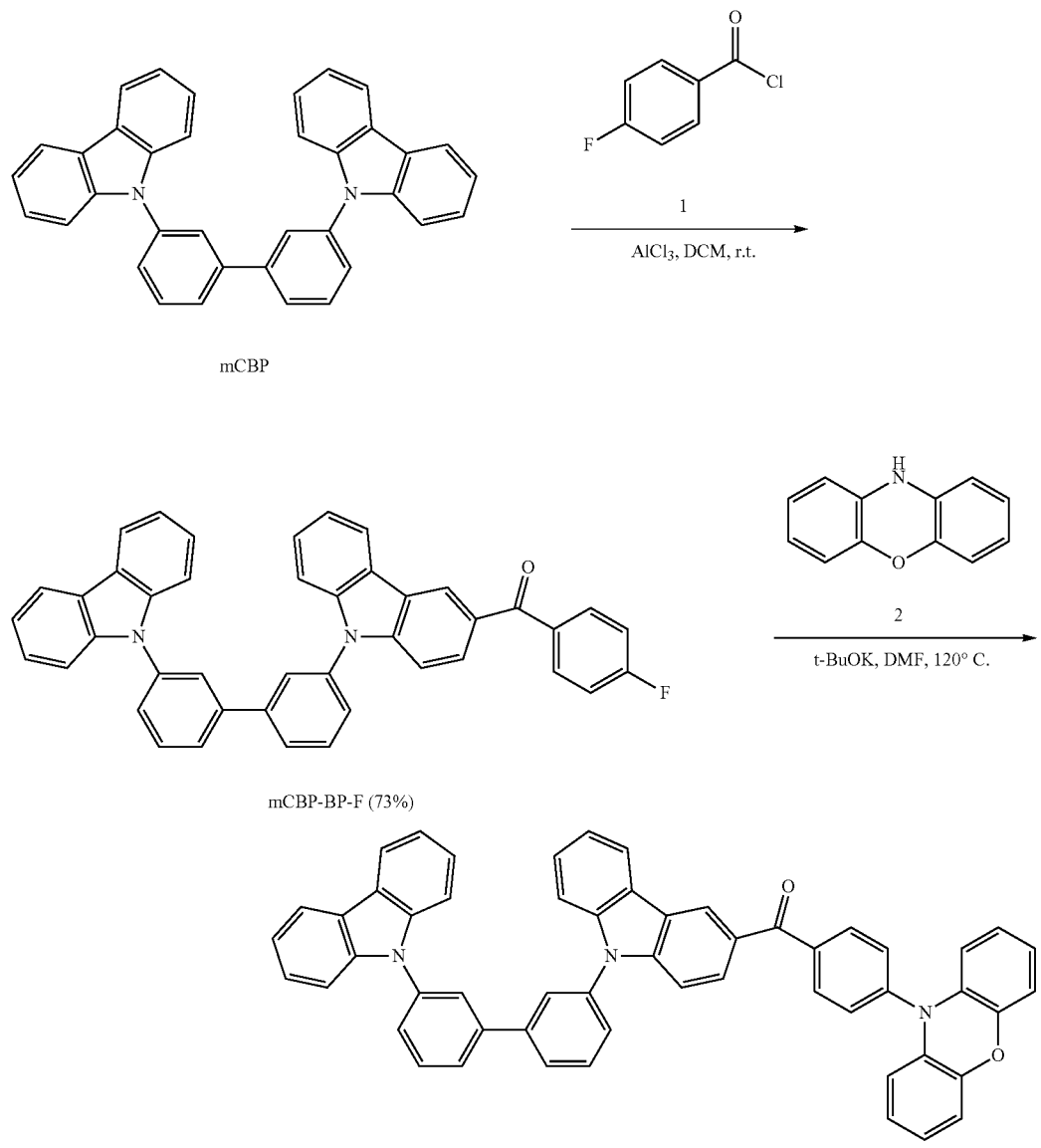

(1) Dissolve p-fluorobenzoyl chloride (0.396 g, 2.5 mmol) and mCBP (1.454 g, 3.0 mmol) in 50 mL of ultra-dry dichloromethane solution, mix well, slowly add AlCl$_3$ (0.467 g, 3.5 mmol), and react at room temperature (in the synthetic route, r.t. means reaction in room temperature) for 3 hours; Then add ice-cold hydrochloric acid solution, extract the product with dichloromethane, concentrate the solution and conduct column chromatography to obtain a white solid mCBP-BP-F with a yield of 73%;

(2) Dissolve the intermediate mCBP-BP-F (0.8 g, 1.2 mmol) and phenoxazine (0.274 g, 1.5 mmol) in 20 mL of ultra-dry DMF, ventilate for three times, add t-BuOK (0.269 g, 2.4 mmol) under nitrogen protection, heat to 120° C., and react at this temperature for 12 hours. Then extract the product with dichloromethane and water, concentrate the solution and conduct column chromatography to obtain a yellow-green final product mCBP-BP-PXZ, the yield being 90%.

$^1$H NMR (500 MHz, CDCl$_3$) δ 8.76 (d, J=1.4 Hz, 1H), 8.22 (d, J=7.8 Hz, 1H), 8.18-8.12 (m, 2H), 8.11-8.05 (m, 2H), 8.02-7.97 (m, 1H), 7.91-7.85 (m, 2H), 7.83-7.78 (m, 1H), 7.78-7.69 (m, 3H), 7.65-7.58 (m, 2H), 7.56-7.33 (m, 10H), 7.33-7.27 (m, 2H), 6.75-6.63 (m, 6H), 6.09-6.00 (m, 2H).

Example 5: Preparation of Carbonyl Containing Organic Electroluminescent Material (TCTA-BP-PXZ)

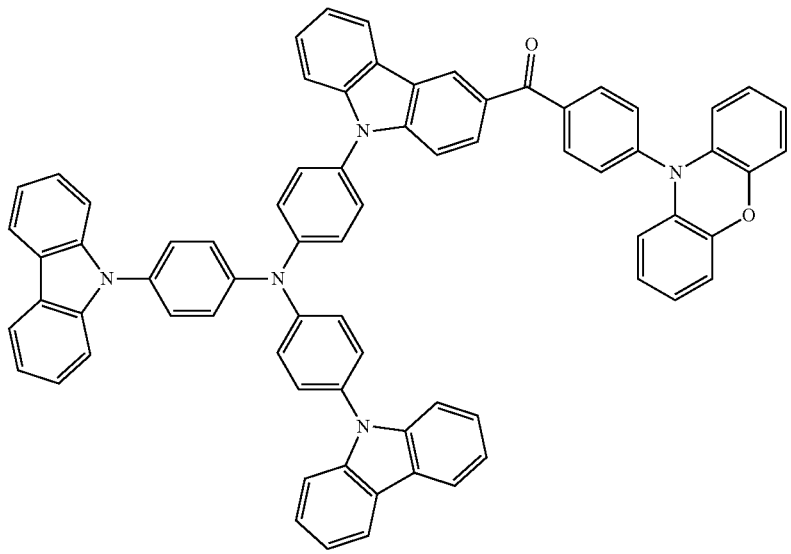 [SMILES: O=C(c1ccc(N2c3ccccc3Oc3ccccc32)cc1)c1ccc2c(c1)c1ccccc1n2-c1ccc(N(c2ccc(-n3c4ccccc4c4ccccc43)cc2)c2ccc(-n3c4ccccc4c4ccccc43)cc2)cc1]

The synthetic route was as follows:

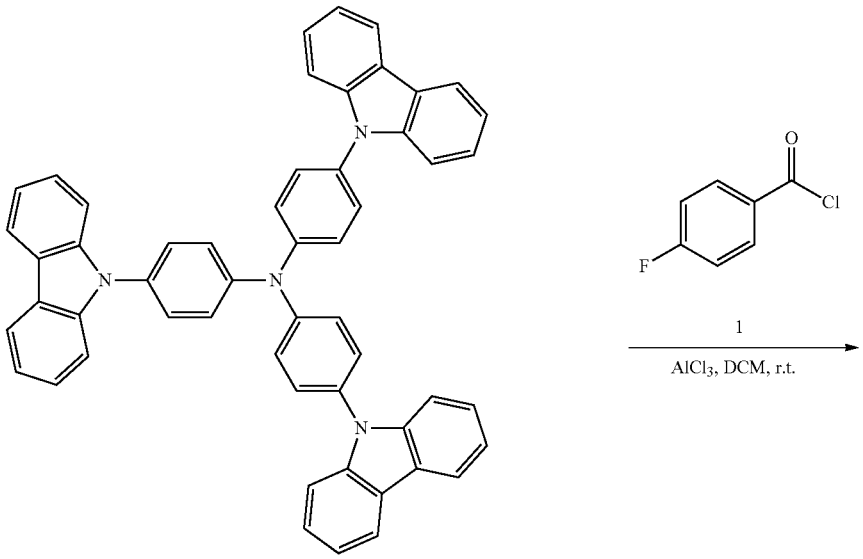

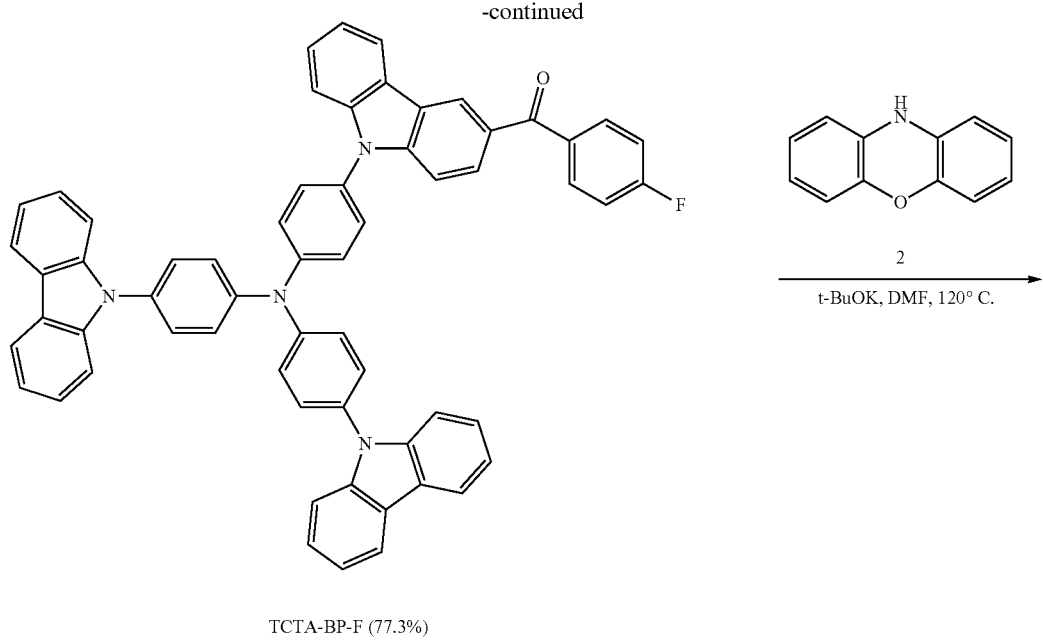

TCTA-BP-F (77.3%)

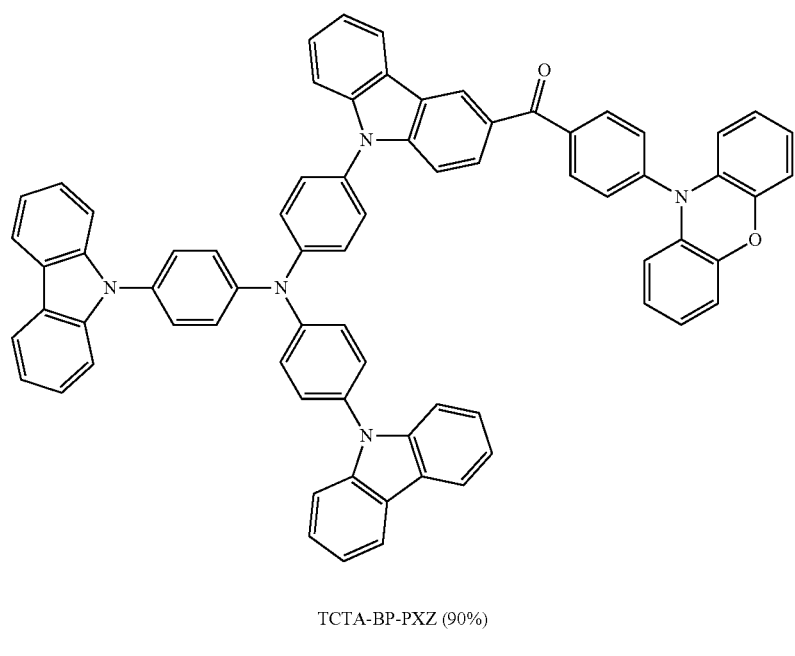 [SMILES: O=C(c1ccc(N2c3ccccc3Oc3ccccc32)cc1)c1ccc2c(c1)c1ccccc1n2-c1ccc(N(c2ccc(-n3c4ccccc4c4ccccc43)cc2)c2ccc(-n3c4ccccc4c4ccccc43)cc2)cc1]

TCTA-BP-PXZ (90%)

(1) Dissolve p-fluorobenzoyl chloride (0.2378 g, 1.50 mmol) and TCTA (2.2268 g, 3.01 mmol) in 50 mL of ultra-dry dichloromethane solution, mix well, slowly add $AlCl_3$ (0.28 g, 2.1 mmol), and react at room temperature (in the synthetic route, r.t. means reaction in room temperature) for 3 hours; Then add ice-cold hydrochloric acid solution, extract the product with dichloromethane, concentrate the solution and conduct column chromatography to obtain a white solid TCTA-BP-F with a yield of 77.3%;

(2) Dissolve the intermediate TCTA-BP-F (1.121 g, 1.3 mmol) and phenoxazine (0.286 g, 1.56 mmol) in 20 mL of ultra-dry DMF, ventilate for three times, add t-BuOK (0.292 g, 2.6 mmol) under nitrogen protection, heat to 120° C., and react at this temperature for 12 hours. Then extract the product with dichloromethane and water, concentrate the solution and conduct column chromatography to obtain a yellow-green final product TCTA-BP-PXZ, the yield being 90%.

HRMS ($C_{73}H_{47}N_5O_2$): m/z 1025.3733 [M+, calcd 1025.3730].

Example 6: Preparation of Carbonyl Containing Organic Electroluminescent Material (TCTA-BP-DMAC)
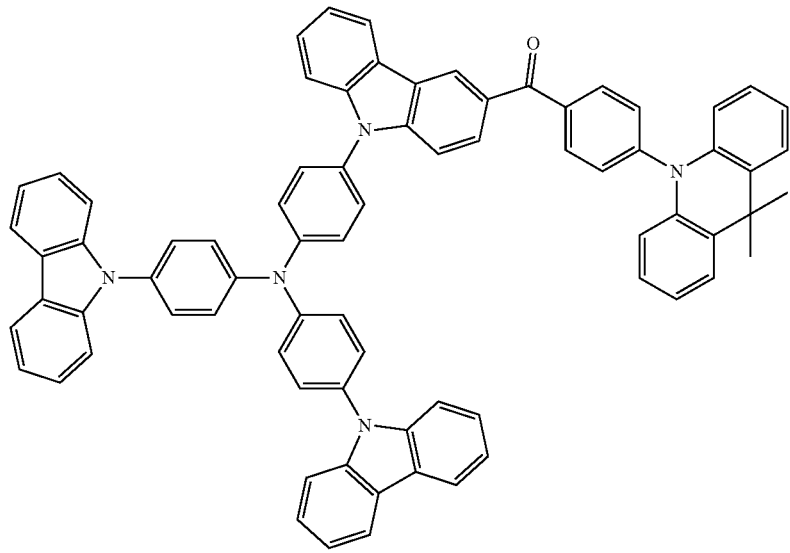 [SMILES: CC1(C)c2ccccc2N(c2ccc(C(=O)c3ccc4c(c3)c3ccccc3n4-c3ccc(N(c4ccc(-n5c6ccccc6c6ccccc65)cc4)c4ccc(-n5c6ccccc6c6ccccc65)cc4)cc3)cc2)c2ccccc21]
The synthetic was as follows:
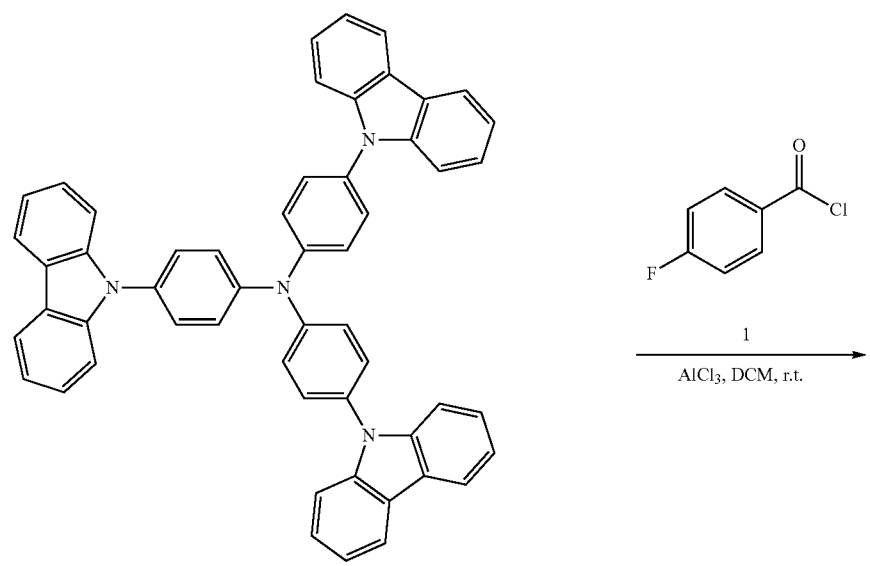
TCTA -continued
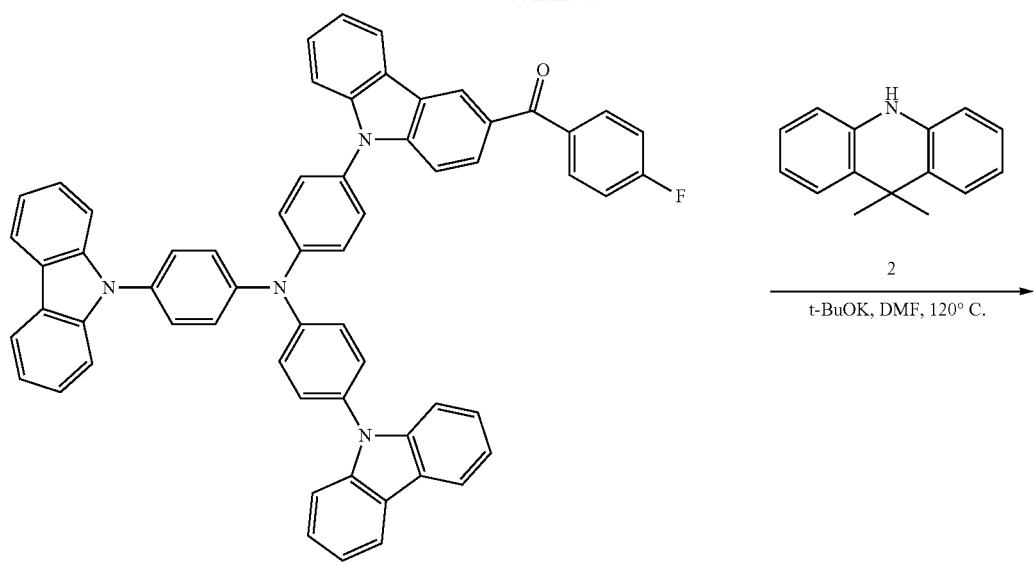
TCTA-BP-F (77.3%)
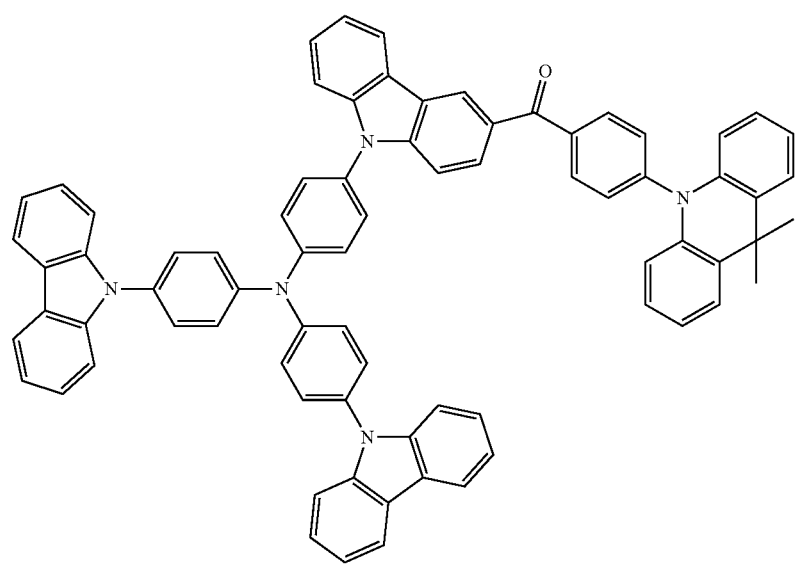
TCTA-BP-DMAC (66.6%)

(1) Dissolve p-fluorobenzoyl chloride (0.2378 g, 1.50 mmol) and TCTA (2.2268 g, 3.01 mmol) in 50 mL of ultra-dry dichloromethane solution, mix well, slowly add $AlCl_3$ (0.28 g, 2.1 mmol), and react at room temperature (in the synthetic route, r.t. means reaction in room temperature) for 3 hours; Then add ice-cold hydrochloric acid solution, extract the product with dichloromethane, concentrate the solution and conduct column chromatography to obtain a white solid TCTA-BP-F with a yield of 77.3%;

(2) Dissolve the intermediate TCTA-BP-F (0.862 μg, 1 mmol) and 9,10-dihydro-9,9-dimethylacridin (0.251 g, 1.2 mmol) in 20 mL of ultra-dry DMF, ventilate for three times, add t-BuOK (0.292 g, 2.6 mmol) under nitrogen protection, heat to 120° C., and react at this temperature for 12 hours. Then extract the product with dichloromethane and water, concentrate the solution and conduct column chromatography to obtain a yellow-green final product TCTA-BP-DMAC, the yield being 66.6%.

HRMS ($C_{76}H_{53}N_5O$): m/z 1051.4280 [M+, calcd 1051.4250].

Example 7: Performance of OLED Device Comprising Carbonyl Containing Organic Electroluminescent Material (DCB-BP-PXZ)

The carbonyl containing organic electroluminescent material DCB-BP-PXZ (solid-state fluorescence quantum yield=69.0%) prepared in Example 1 was used as a luminescent material to prepare doped devices and non-doped devices. Tests and characterizations have been done, and the results are shown in FIG. 1-2.

Device structure: ITO/TAPC (25 nm)/emitter (30 wt %): CBP (35 nm)/TmPyPB (55 nm)/LiF (1 nm)/Al (doped OLED); ITO/TAPC (25 nm)/emitter (35 nm)/TmPyPB (55 nm)/LiF (1 nm)/Al (non-doped OLED).

FIG. 1 is a J-V-L curve diagram of the doped and undoped OLEDs prepared by the carbonyl containing organic electroluminescent material in Example 1. It can be seen from the figure that the DCB-BP-PXZ-based doped and undoped devices have high maximum luminance and low starting voltage, which are respectively 91981 $cd/m^2$, 2.7 V and 95577 $cd/m^2$, 2.5 V.

Figure 2:
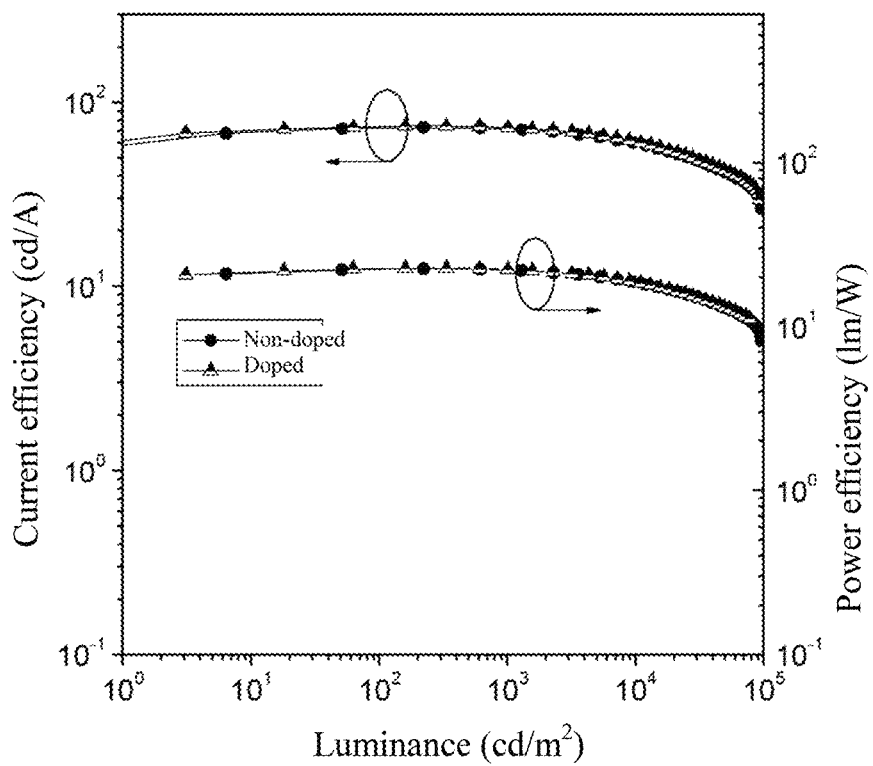
FIG. 2 is a graph showing the change in efficiency of doped and non-doped OLEDs devices prepared by the carbonyl containing organic electroluminescent materials in Example 1 with luminance.

FIG. 2 is a graph showing the change in the efficiency of the doped and non-doped OLEDs prepared by the carbonyl containing organic electroluminescent material in Example 1 with luminance. It can be seen from the figure that both doped and undoped devices based on DCB-BP-PXZ have good efficiency and low roll-off.

The maximum current efficiency and external quantum efficiency are 74.1 cd/A, 22.7% and 72.9 cd/A, 22.6%, respectively; when the luminance is 100 $cd/m^2$, the external quantum efficiencies are maintained at 22.4% and 22.1%, respectively; when the luminance is 1000 $cd/m^2$, the external quantum efficiencies are 22.0% and 21.5%, respectively; and when the luminance is 10000 $cd/m^2$, the external quantum efficiencies are 18.8% and 18.7%, respectively.

Example 8: Performance of OLED Device Comprising Carbonyl Containing Organic Electroluminescent Material (CBP-BP-PXZ)

The carbonyl containing organic electroluminescent material CBP-BP-PXZ (solid-state fluorescence quantum yield=71.6%) prepared in Example 2 was used as a luminescent material to prepare doped and non-doped devices. Tests and characterizations have been done, and the results are shown in FIGS. 3 and 4.

Device structure: ITO/TAPC (25 nm)/emitter (30 wt %): CBP (35 nm)/TmPyPB (55 nm)/LiF (1 nm)/Al (doped structure);

ITO/TAPC (25 nm)/emitter (35 nm)/TmPyPB (55 nm)/LiF (1 nm)/Al (non-doped structure).

Figure 3:
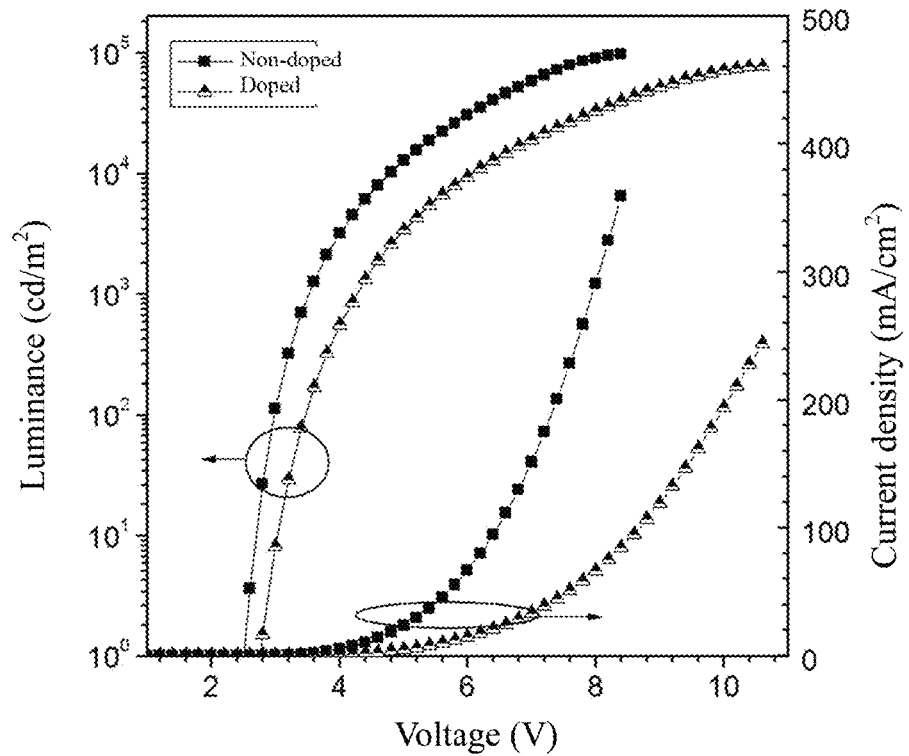
FIG. 3 is a J-V-L curve diagram of doped and undoped OLEDs prepared by the carbonyl containing organic electroluminescent materials in Example 2.
Figure 4:
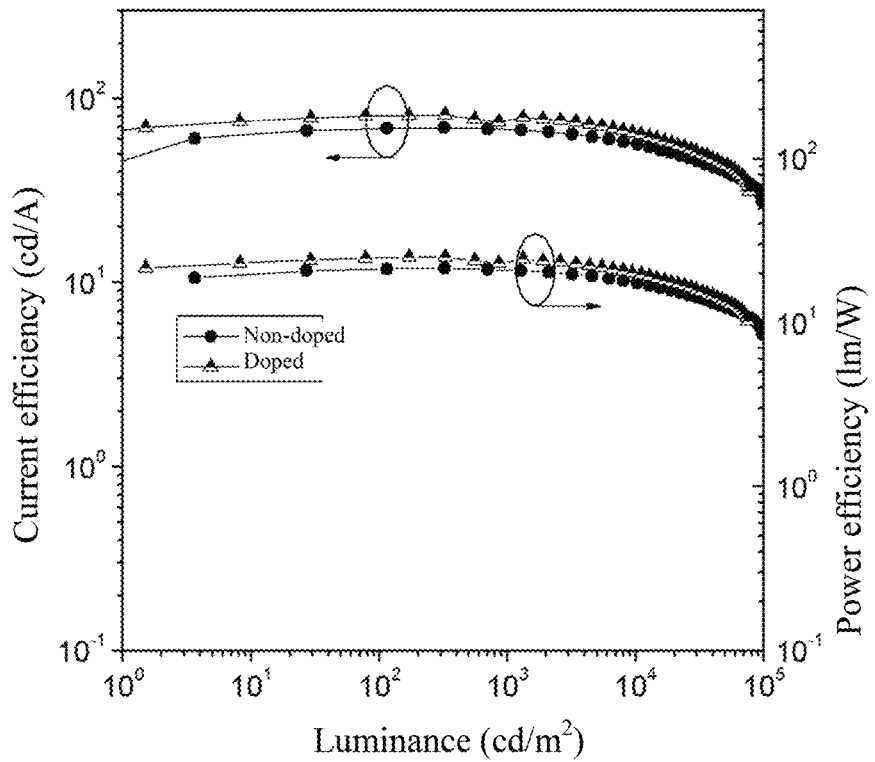
FIG. 4 is a graph showing the change in efficiency of doped and non-doped OLEDs devices prepared by the carbonyl containing organic electroluminescent materials in Example 2 with luminance.

FIG. 3 is a J-V-L curve diagram of doped and undoped OLEDs prepared by the carbonyl containing organic electroluminescent material in Example 2. It can be seen from the figure that the maximum luminance of the doped and undoped devices based on CBP-BP-PXZ is high and the starting voltage is low, which are respectively 76488 $cd/m^2$, 2.7 V and 98089 $cd/m^2$, 2.5 V.

FIG. 4 is a graph showing the change in the efficiency of the doped and non-doped OLEDs prepared by the carbonyl containing organic electroluminescent material in Example 2 with luminance. It can be seen from the figure that both doped and undoped devices based on CBP-BP-PXZ have good efficiency and low roll-off.

The maximum current efficiency and external quantum efficiency are 81.2 cd/A, 25.1% and 69.0 cd/A, 21.4%, respectively; when the luminance is 100 $cd/m^2$, the external quantum efficiencies are 24.8% and 21.1%, respectively; when the luminance is 1000 $cd/m^2$, the external quantum efficiencies are 23.6% and 21.0%, respectively; when the luminance is 10000 $cd/m^2$, the external quantum efficiencies are 20.0% and 17.5%, respectively.

Example 9: Performance of OLED Device Comprising Carbonyl Containing Organic Electroluminescent Material (mCP-BP-PXZ)

The carbonyl containing organic electroluminescent material mCP-BP-PXZ (solid-state fluorescence quantum yield=66.0%) prepared in Example 3 was used as a luminescent material to prepare doped and non-doped devices. Tests and characterizations have been done, and the results are shown in FIGS. 5-6.

Device structure: ITO/TAPC (25 nm)/emitter (30 wt %): CBP (35 nm)/TmPyPB (55 nm)/LiF (1 nm)/Al (doped structure);

ITO/TAPC (25 nm)/emitter (35 nm)/TmPyPB (55 nm)/LiF (1 nm)/Al (non-doped structure).

Figure 5:
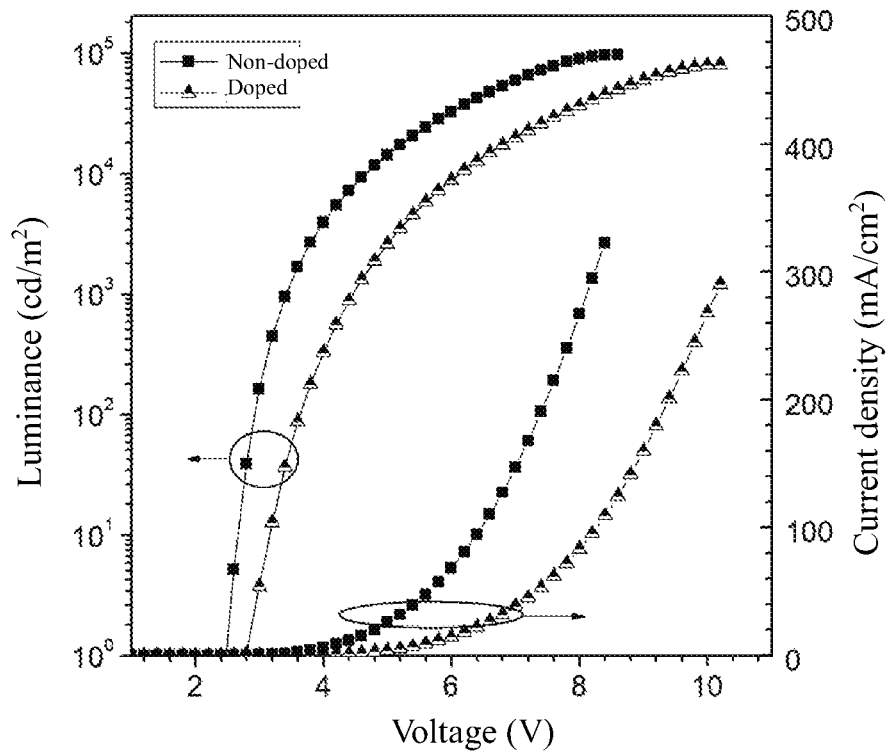
FIG. 5 is a J-V-L curve diagram of doped and undoped OLEDs prepared by the carbonyl containing organic electroluminescent materials in Example 3.
Figure 6:
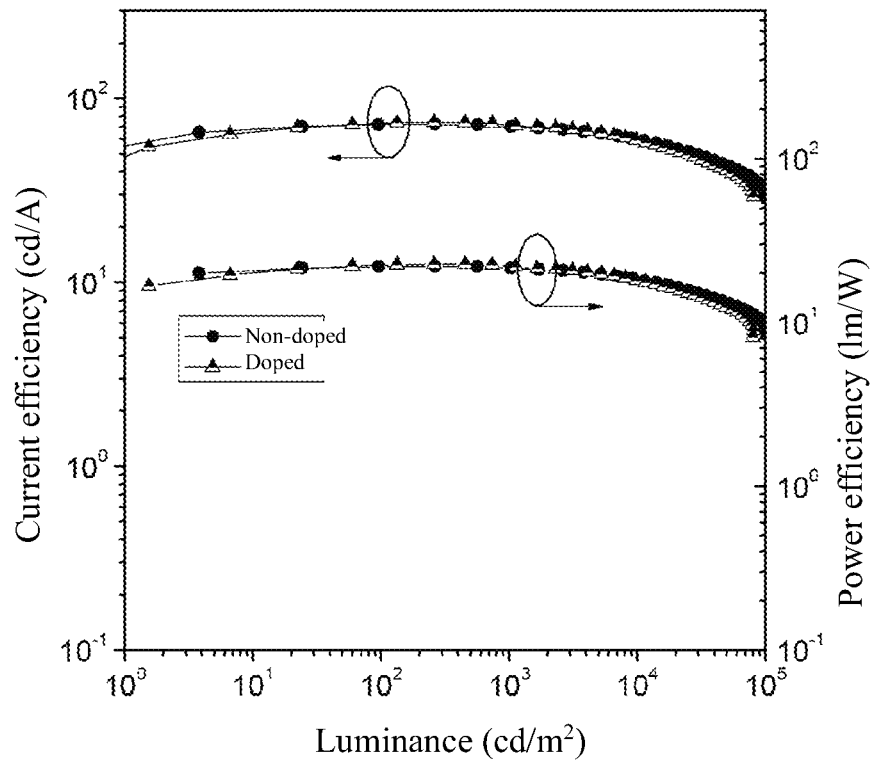
FIG. 6 is a graph showing the change in efficiency of doped and non-doped OLEDs devices prepared by the carbonyl containing organic electroluminescent materials in Example 3 with luminance.

FIG. 5 is a J-V-L curve diagram of doped and undoped OLEDs prepared by the carbonyl containing organic electroluminescent material in Example 3. It can be seen from the figure that the doped and undoped devices based on mCP-BP-PXZ have high maximum luminance and low starting voltage, which are respectively 80873 $cd/m^2$, 2.7 V and 100126 $cd/m^2$, 2.5 V.

FIG. 6 is a graph showing the change in the efficiency of the doped and non-doped OLEDs prepared by the carbonyl containing organic electroluminescent material in Example 3 with luminance. It can be seen from the figure that both doped and undoped devices based on mCP-BP-PXZ have good efficiency and low roll-off. The maximum current efficiency and external quantum efficiency are 74.3 cd/A, 22.7% and 72.3 cd/A, 22.1%, respectively; when the luminance is 100 cd/m², the external quantum efficiencies are 24.8% and 21.2%, respectively; when the luminance is 1000 cd/m², the external quantum efficiencies are 23.6% and 21.0%, respectively; when the luminance is 10000 cd/m², the external quantum efficiencies are 18.1% and 18.4%, respectively.

Example 10: Performance of OLED Device Comprising Carbonyl Containing Organic Electroluminescent Material (mCBP-BP-PXZ)

The carbonyl containing organic electroluminescent material mCBP-BP-PXZ (solid-state fluorescence quantum yield=71.2%) prepared in Example 4 was used as a luminescent material to prepare doped and non-doped devices. Tests and characterizations have been done, and the results are shown in FIGS. 7-8.

Device structure: ITO/TAPC (25 nm)/emitter (30 wt %): CBP (35 nm)/TmPyPB (55 nm)/LiF (1 nm)/Al (doped structure);

ITO/TAPC (25 nm)/emitter (35 nm)/TmPyPB (55 nm)/LiF (1 nm)/Al (non-doped structure).

Figure 7:
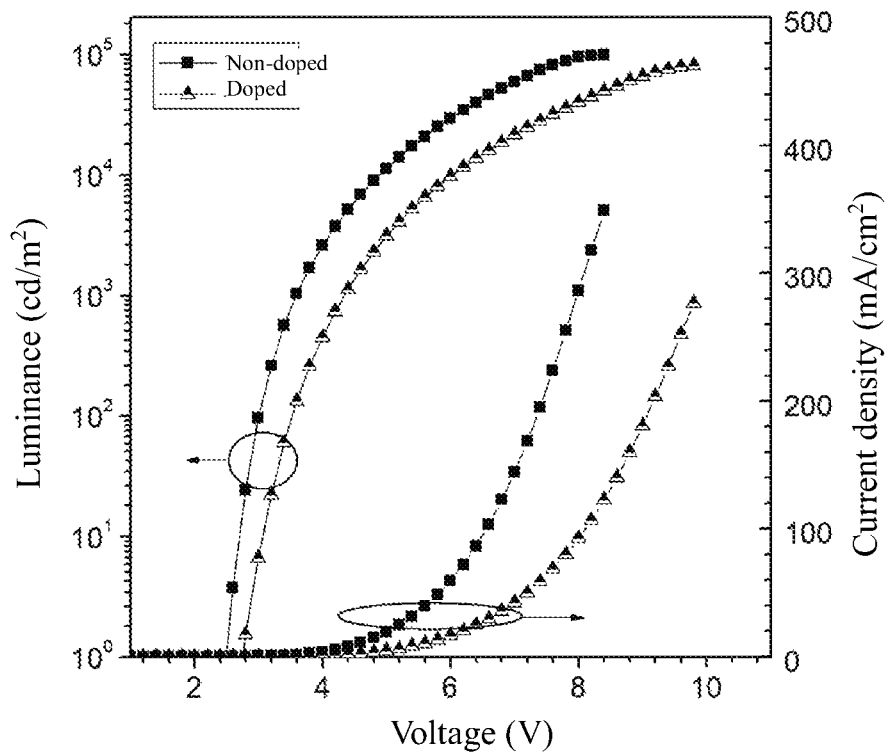
FIG. 7 is a J-V-L curve diagram of doped and undoped OLEDs prepared by the carbonyl containing organic electroluminescent materials in Example 4.
Figure 8:
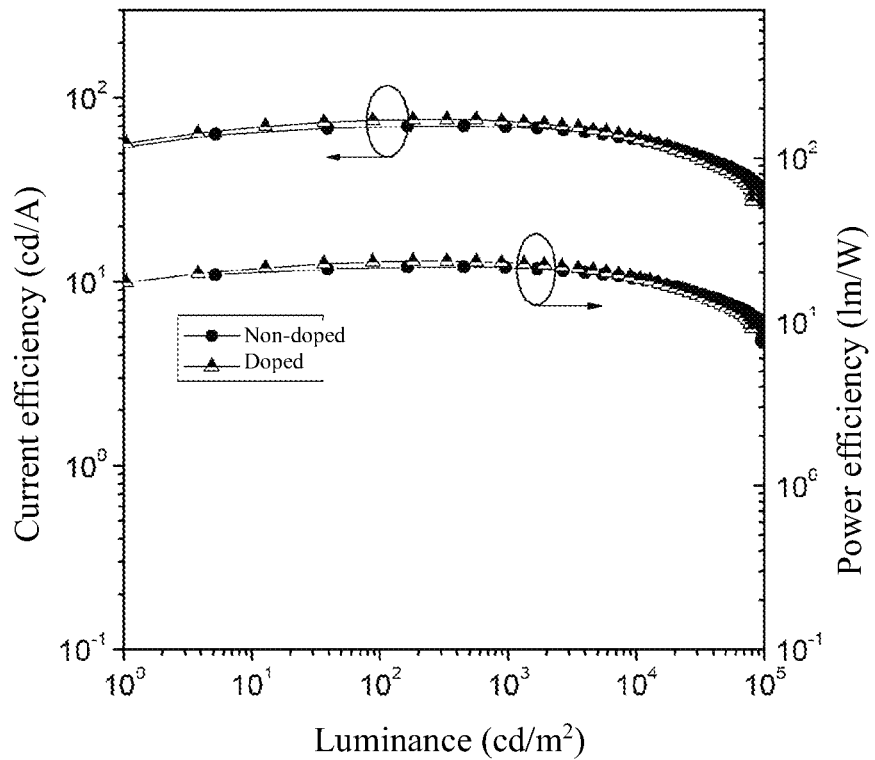
FIG. 8 is a graph showing the change in efficiency of doped and non-doped OLEDs devices prepared by the carbonyl containing organic electroluminescent materials in Example 4 with luminance.

FIG. 7 is a J-V-L curve diagram of doped and undoped OLEDs prepared by the carbonyl containing organic electroluminescent material in Example 4. It can be seen from the figure that the maximum luminance of doped and undoped devices based on mCBP-BP-PXZ is high and the starting voltage is low, which are respectively 79644 cd/m², 2.7 V and 96815 cd/m², 2.5 V.

FIG. 8 is a graph of the efficiency of the doped and non-doped OLEDs prepared by the carbonyl containing organic electroluminescent material in Example 4 with luminance. It can be seen from the figure that both doped and undoped devices based on mCP-BP-PXZ have good efficiency and low roll-off. The maximum current efficiency and external quantum efficiency are 76.3 cd/A, 23.5% and 76.5 cd/A, 21.8%, respectively; when the luminance is 100 cd/m², the external quantum efficiencies are 22.6% and 22.5%, respectively; when the luminance is 1000 cd/m², the external quantum efficiencies are 22.4% and 22.2%, respectively; when the luminance is 10000 cd/m², the external quantum efficiencies are 18.5% and 18.3%, respectively.

The above data shows that the present disclosure obtains molecules with both AIE and delayed fluorescence characteristics by attaching different electron-donating groups on both sides of the benzoyl group. The doped OLEDs prepared by using such materials as a light-emitting layer have high efficiency and low roll-off. Non-doped OLEDs devices with simple structures prepared based on such materials have lower starting voltage, higher efficiency, and a smaller degree of efficiency roll-off. In short, this type of material has a very broad application prospect in the field of organic electroluminescence.

The above-mentioned embodiments are preferred embodiments of the present disclosure, but the embodiments of the present disclosure are not limited by the above-mentioned embodiments, and any other changes, modifications, substitutions, combinations, and simplifications made without departing from the spirit and principle of the present disclosure all should be equivalent replacement methods and are all included in the protection scope of the present disclosure.

The invention claimed is:

1. A carbonyl containing organic electroluminescent material having one of the following structures:

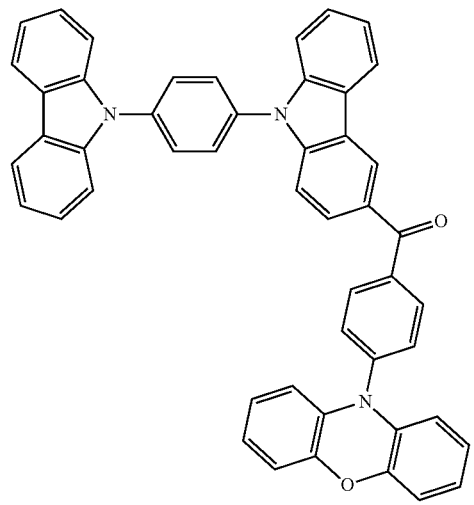

1

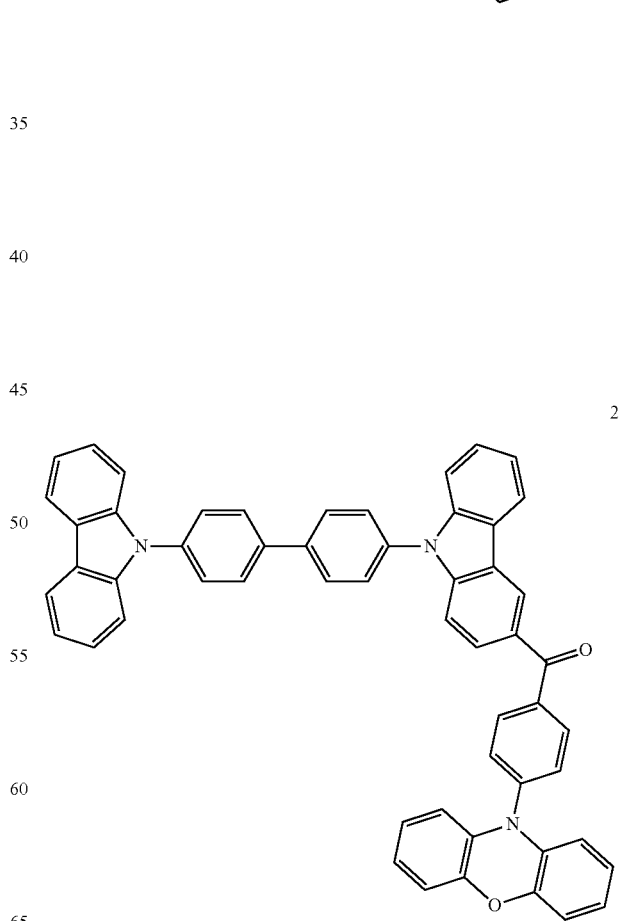

2

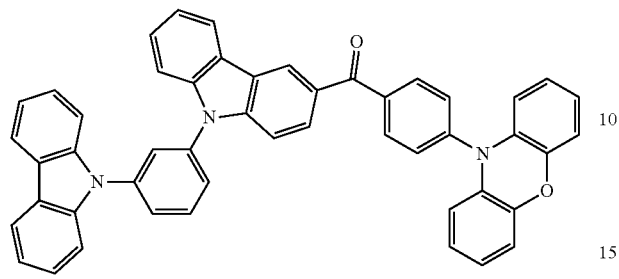

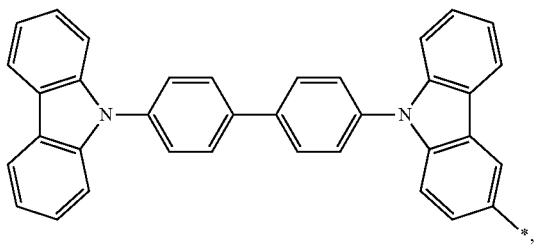

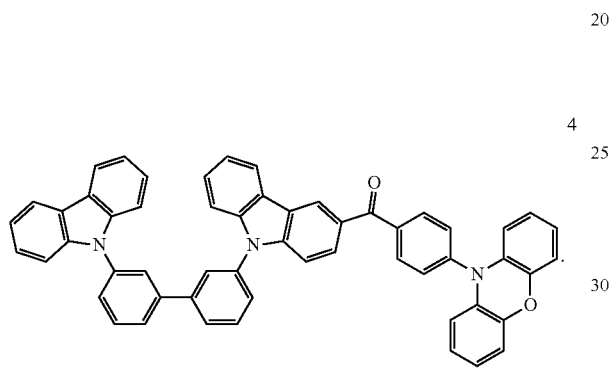

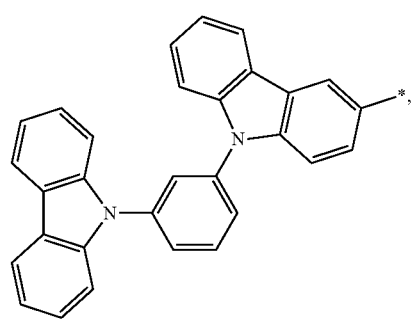

2. A method of preparing the carbonyl containing organic electroluminescent material according to claim 1, comprising the following steps:

using p-fluorobenzoyl chloride and an aromatic derivative R₁H as raw materials, obtaining organic fluoride through a Friedel-Crafts reaction; and under the action of a strong base catalyst, carrying out a reaction between the organic fluoride and an aromatic derivative R₂H to obtain the carbonyl containing organic electroluminescent material, wherein R₁H has one of the following structures:

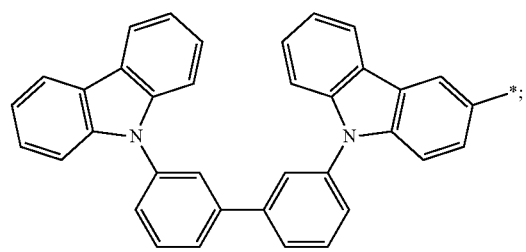

and wherein R₂H has the following structure:

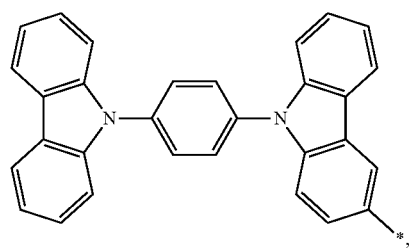

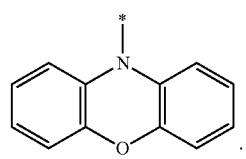 [SMILES: *N1c2ccccc2Oc2ccccc21]

3. The carbonyl containing organic electroluminescent material according to claim 1, wherein the material has the following structure:

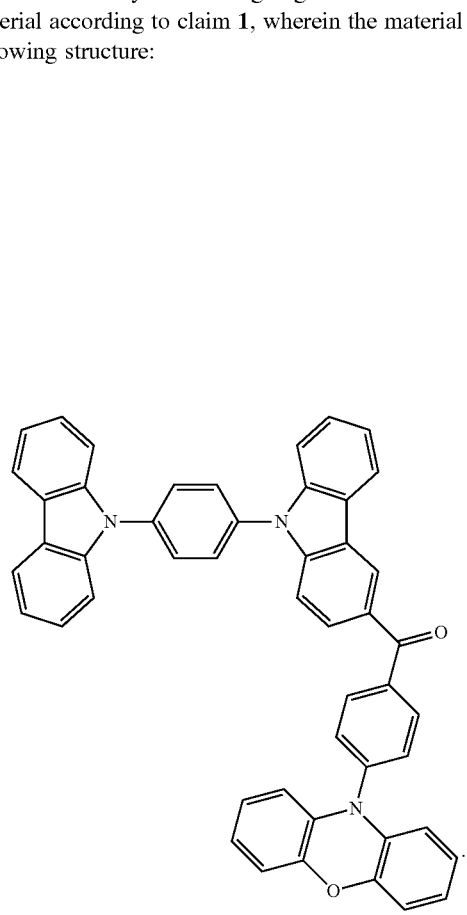

4. The carbonyl containing organic electroluminescent material according to claim 1, wherein the material has the following structure:

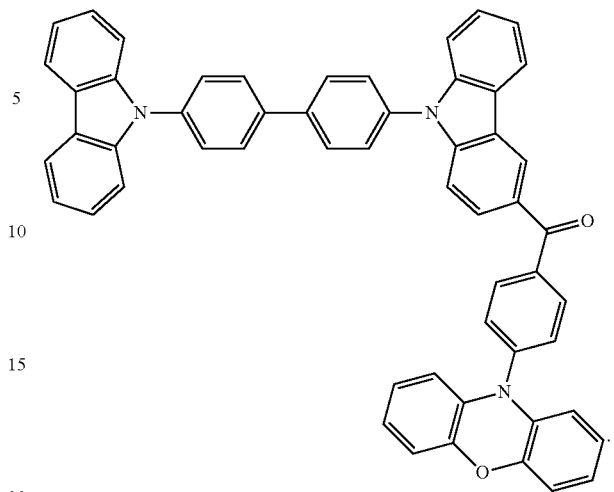

5. The carbonyl containing organic electroluminescent materials according to claim 1, wherein the material has the following structure:

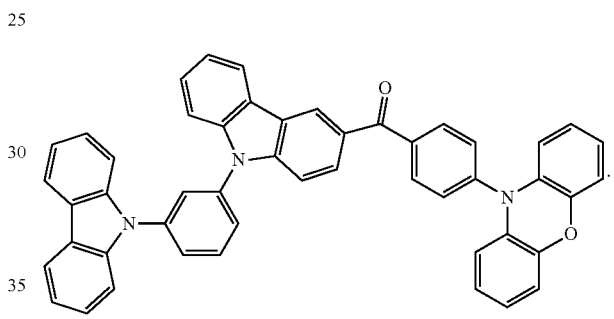

6. The carbonyl containing organic electroluminescent material according to claim 1, wherein the material has the following structure:

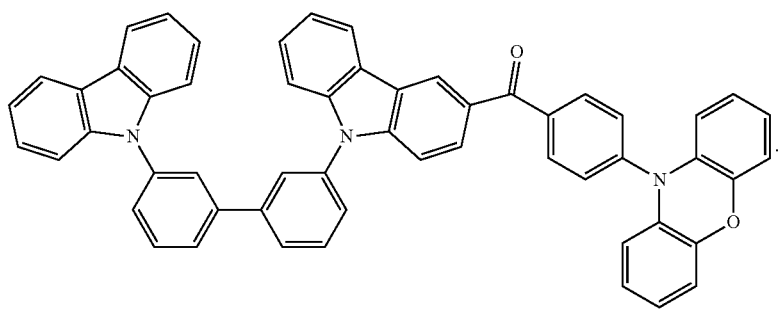 [SMILES: O=C(c1ccc(N2c3ccccc3Oc3ccccc32)cc1)c1ccc2c(c1)c1ccccc1n2-c1cccc(-c2cccc(-n3c4ccccc4c4ccccc43)c2)c1]

7. An organic electroluminescent device comprising the carbonyl containing organic electroluminescent material of claim 1.

\* \* \* \* \*